(12) United States Patent
Koenck et al.

(10) Patent No.: US 6,885,011 B2
(45) Date of Patent: Apr. 26, 2005

(54) IRRADIATION SYSTEM AND METHOD

(75) Inventors: Steven E. Koenck, Cedar Rapids, IA (US); Stan V. Lyons, Brentwood, CA (US); Brian T. Dalziel, Marion, IA (US); Douglas C. White, Cedar Rapids, IA (US); Janette J. Kewley, Marion, IA (US); Von Kennedy, Cedar Rapids, IA (US)

(73) Assignee: Mitec Incorporated, Cedar Rapids, IA (US)

( * ) Notice: Subject to any disclaimer, the term of this patent is extended or adjusted under 35 U.S.C. 154(b) by 0 days.

(21) Appl. No.: 10/115,507

(22) Filed: Apr. 2, 2002

(65) Prior Publication Data

US 2002/0162971 A1 Nov. 7, 2002

Related U.S. Application Data

(60) Provisional application No. 60/280,790, filed on Apr. 2, 2001, provisional application No. 60/333,045, filed on Nov. 14, 2001, and provisional application No. 60/359,813, filed on Feb. 26, 2002.

(51) Int. Cl.$^7$ ................................................ G21K 5/10
(52) U.S. Cl. ................................................ 250/455.11
(58) Field of Search ...................... 250/455.11, 492.3

(56) References Cited

U.S. PATENT DOCUMENTS

| | | | |
|---|---|---|---|
| 924,284 A | 6/1909 | Smith | |
| 1,809,078 A | 6/1931 | Smith | |
| 2,095,502 A | 10/1937 | Johnston | 21/54 |
| 2,456,909 A | * 12/1948 | Brasch | 422/22 |
| 2,602,751 A | 7/1952 | Robinson | 99/221 |
| 2,741,704 A | 4/1956 | Trump et al. | 250/49.5 |
| 2,816,231 A | 12/1957 | Nygard | 250/43 |
| 2,824,969 A | 2/1958 | Crowley-Milling | 250/49.5 |
| 2,963,369 A | 12/1960 | Urbain | 99/107 |
| 2,989,735 A | 6/1961 | Gumpertz | 340/174.1 |
| 3,087,598 A | 4/1963 | Clore | 198/38 |
| 3,224,562 A | 12/1965 | Bailey et al. | 198/131 |
| 3,261,140 A | 7/1966 | Long et al. | 53/22 |
| 3,396,273 A | 8/1968 | Brunner | 250/52 |
| 3,452,195 A | 6/1969 | Brunner | 250/52 |
| 3,560,745 A | 2/1971 | Petersen et al. | 250/83 |
| 3,564,241 A | 2/1971 | Ludwig | 250/52 |
| 3,567,462 A | 3/1971 | Silverman et al. | 99/157 |
| 3,676,673 A | 7/1972 | Coleman | 250/49.5 |
| 3,676,675 A | 7/1972 | Ransohoff et al. | 250/52 |
| 3,780,305 A | 12/1973 | Free | 250/400 |
| 3,876,373 A | 4/1975 | Glyptis | 21/54 |
| 3,974,391 A | 8/1976 | Offermann | 250/492 |
| 4,013,261 A | 3/1977 | Steigerwald et al. | 250/453 |
| 4,066,907 A | 1/1978 | Tetzlaff | 250/453 |
| 4,151,419 A | 4/1979 | Morris et al. | 250/453 |
| 4,201,920 A | 5/1980 | Tronc et al. | 250/492 |
| 4,281,251 A | 7/1981 | Thompson et al. | 250/398 |
| 4,296,068 A | 10/1981 | Hoshino | |
| 4,484,341 A | 11/1984 | Luniewski | 378/69 |
| 4,652,763 A | 3/1987 | Nablo | 250/492.3 |
| 4,663,532 A | 5/1987 | Roche | 250/400 |
| 4,713,252 A | 12/1987 | Ismail | |
| 4,757,201 A | 7/1988 | Kanter | 250/337 |
| 4,760,264 A | 7/1988 | Barrett | 250/453.1 |
| 4,767,930 A | 8/1988 | Stieber et al. | 250/396 |
| 4,785,178 A | 11/1988 | Lynch et al. | 250/496.1 |
| 4,788,126 A | 11/1988 | Feldman et al. | 430/138 |

(Continued)

*Primary Examiner*—John R. Lee
*Assistant Examiner*—Phillip A Johnston
(74) *Attorney, Agent, or Firm*—Kinney & Lange, P.A.

(57) ABSTRACT

An irradiation system includes a conveying system for moving material to be irradiated through a processing area. An irradiation source applies radiation to material in the processing area. The conveying system is enclosed by a sealed conduit in at least the processing area, providing the capability to control the atmosphere inside the sealed conduit and to clean the interior of the sealed conduit according to industrial sanitation methods.

33 Claims, 21 Drawing Sheets

U.S. PATENT DOCUMENTS

| | | | |
|---|---|---|---|
| 4,788,701 A | 11/1988 | Barrett | 378/69 |
| 4,852,138 A | 7/1989 | Bergeret et al. | 378/69 |
| 4,864,595 A | 9/1989 | Barrett | 378/69 |
| 4,866,281 A | 9/1989 | Bosshard | 250/453.1 |
| 4,870,368 A | 9/1989 | Putnam | 328/233 |
| 4,908,221 A | 3/1990 | Barrett | 426/240 |
| 4,974,503 A | 12/1990 | Koch | 99/451 |
| 5,004,926 A | 4/1991 | Vassenaix et al. | 250/492.3 |
| 5,008,550 A | 4/1991 | Barrett | 250/453.1 |
| 5,026,983 A | 6/1991 | Meyn | 250/233 R |
| 5,096,553 A | 3/1992 | Ross et al. | 204/157.15 |
| 5,101,168 A | 3/1992 | Miller | 328/233 |
| 5,323,442 A | 6/1994 | Golovanivsky et al. | 378/119 |
| 5,362,442 A | 11/1994 | Kent | 422/22 |
| 5,366,746 A | 11/1994 | Mendenhall | 426/521 |
| 5,396,071 A | 3/1995 | Atwell et al. | 250/358.1 |
| 5,396,074 A | 3/1995 | Peck et al. | 250/453.11 |
| 5,400,382 A | 3/1995 | Welt et al. | 378/69 |
| 5,434,421 A | 7/1995 | Burth | 250/434 |
| 5,451,790 A | 9/1995 | Enge | 250/436 |
| 5,461,656 A | 10/1995 | Golovanivsky et al. | 378/66 |
| 5,470,597 A | 11/1995 | Mendenhall | 426/521 |
| 5,482,726 A | 1/1996 | Robinson, Jr. | 426/238 |
| 5,530,255 A | 6/1996 | Lyons et al. | 250/492.3 |
| 5,554,856 A | 9/1996 | Bidnyy et al. | 250/455 |
| 5,557,109 A | 9/1996 | Bidnyy et al. | 250/455 |
| 5,590,602 A | 1/1997 | Peck et al. | 104/88.01 |
| 5,593,713 A | 1/1997 | De La Luz-Martinez et al. | 426/237 |
| 5,597,597 A | 1/1997 | Newman | 426/248 |
| 5,597,599 A | 1/1997 | Smith et al. | |
| 5,603,972 A * | 2/1997 | McFarland | 426/240 |
| 5,635,714 A | 6/1997 | Nablo et al. | 250/305 |
| 5,661,305 A | 8/1997 | Lawrence et al. | 250/397 |
| 5,690,978 A | 11/1997 | Yin et al. | 426/237 |
| 5,712,894 A * | 1/1998 | Lanotte | 378/68 |
| 5,801,387 A | 9/1998 | Nablo et al. | 250/492.3 |
| 5,834,744 A | 11/1998 | Risman | 219/697 |
| 5,838,760 A | 11/1998 | Moses | 378/119 |
| 5,847,401 A | 12/1998 | McKeown et al. | 250/396 |
| 5,881,534 A | 3/1999 | Ahlqvist et al. | 53/403 |
| 5,994,706 A | 11/1999 | Allen et al. | 250/454.11 |
| 6,023,497 A | 2/2000 | Takahashi et al. | 378/57 |
| 6,027,754 A | 2/2000 | Bushnell et al. | 426/238 |
| 6,051,185 A | 4/2000 | Beers | 422/22 |
| 6,066,348 A | 5/2000 | Yuan et al. | 426/236 |
| 6,086,932 A | 7/2000 | Gupta | 426/237 |
| 6,096,379 A | 8/2000 | Eckhoff | 427/428 |
| 6,127,687 A | 10/2000 | Williams et al. | 250/492.3 |
| 6,215,847 B1 * | 4/2001 | Perrins | 378/69 |
| 6,429,444 B1 | 8/2002 | Korenev et al. | 250/492.3 |

* cited by examiner

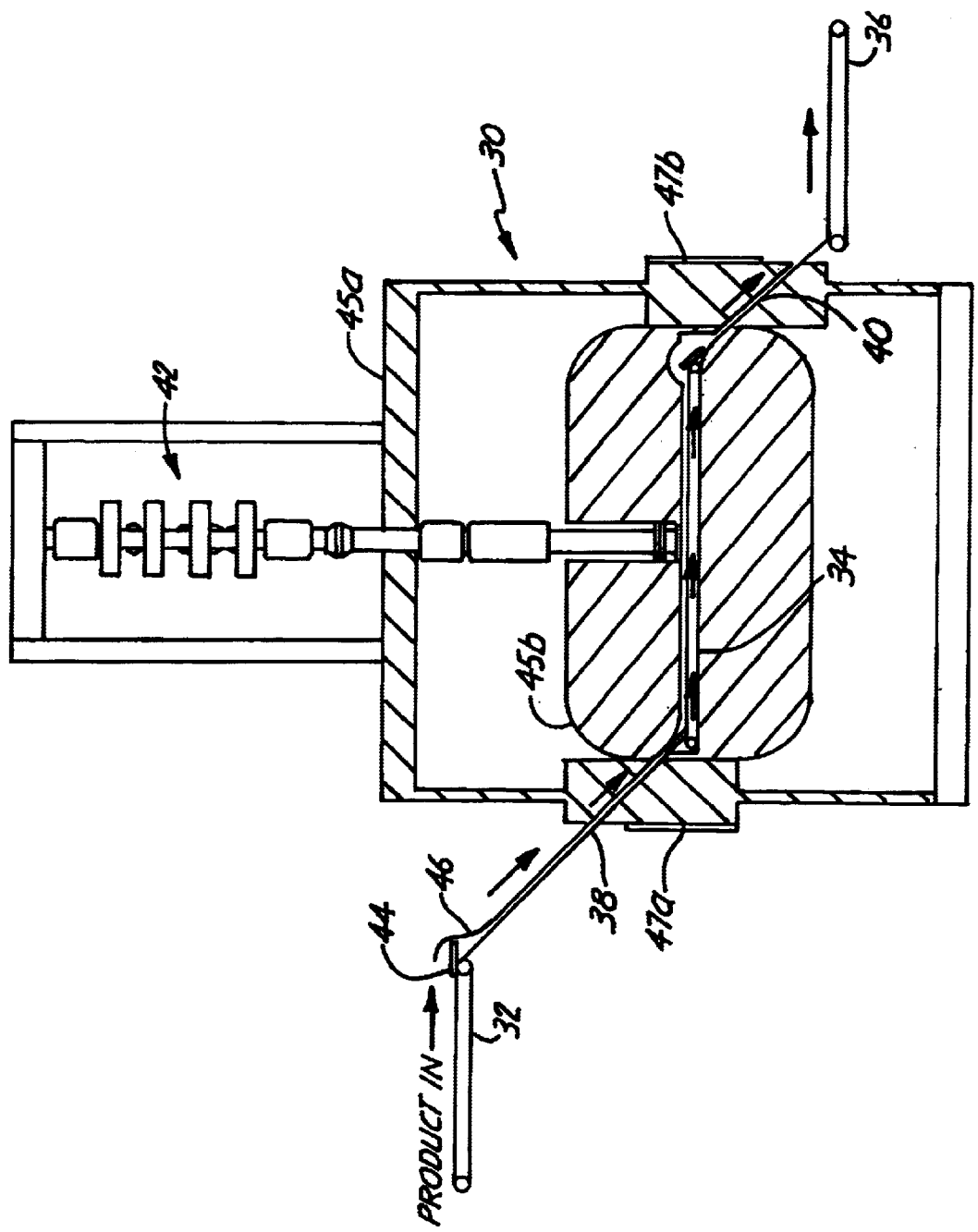

IRRADIATION SYSTEM AND METHOD

CROSS-REFERENCE TO RELATED APPLICATION(S)

This application claims the benefit of Provisional Application No. 60/280,790 filed Apr. 2, 2001 for "Irradiation System for Food or Other Articles" by S. Lyons, S. Koenck, B. Dalziel, D. White and J. Kewley, and also claims the benefit of Provisional Application No. 60/333,045 filed Nov. 14, 2001 for "Irradiation System for Sanitizing Mail" by S. Lyons, S. Koenck, B. Dalziel and V. Kennedy, and also claims the benefit of Provisional Application No. 60/359,813 filed Feb. 26, 2002 for "Irradiation System for Stationary Articles" by S. Lyons, S. Koenck, B. Dalziel and V. Kennedy.

INCORPORATION BY REFERENCE

The aforementioned Provisional Application Nos. 60/280,790, 60/333,045 and 60/359,813 are hereby incorporated by reference in their entirety. In addition, U.S. application Ser. No. 09/685,799 filed Oct. 10, 2000 for "Irradiation System and Method" by S. Lyons, S. Koenck, B. Dalziel and J. Kewley and U.S. application Ser. No. 09/795,058 filed Feb. 26, 2001 for "Bulk Material Irradiation System and Method" by S. Lyons, S. Koenck, B. Dalziel, D. White and J. Kewley are also hereby incorporated by reference in their entirety.

BACKGROUND OF THE INVENTION

The present invention relates to an irradiation system and method, and more particularly to a system for irradiating material inside a sealed conduit that houses a conveying system.

Irradiation technology for medical and food sterilization has been scientifically understood for many years dating back to the 1940's. The increasing concern for food safety as well as safe, effective medical sterilization has resulted in growing interest and recently expanded government regulatory approval of irradiation technology for these applications. United States Government regulatory agencies have recently approved the use of irradiation processing of red meat in general and ground meat in particular. Ground meat such as ground beef is of particular concern for risk of food borne illness due to the fact that contaminants introduced during processing may be mixed throughout the product including the extreme product interior which receives the least amount of heat during cooking. Irradiation provides a very effective means of reducing the population of such harmful pathogens.

The available sources of ionizing radiation for irradiation processing consist primarily of gamma sources, high energy electrons and x-ray radiation. The most common gamma source for irradiation purposes is radioactive cobalt 60 which is simple and effective but expensive and hazardous to handle, transport, store and use. For these reasons, electron beam and x-ray generation are becoming the preferred technologies for material irradiation. An exemplary maximum electron beam energy for irradiation purposes is on the order of 10 million electron-volts (MeV) which results in effective irradiation without causing surrounding materials to become radioactive. The necessary electron beam power must be on the order of 5 to 10 kilowatts or more to effectively expose materials at rates sufficient for industrial processing.

Electron beam and x-ray irradiation systems both employ an electron accelerator to either emit high velocity electrons directly for irradiation or to cause high velocity electrons to collide with a metal conversion plate which results in the emission of x-rays. A number of electron acceleration techniques have been developed over the past several decades including electrostatic acceleration, pumped cylindrical accelerators and linear accelerators.

Electrostatic accelerators are characterized by the use of a direct current static voltage of typically 30 to 90 kilovolts which accelerates electrons due to charge attraction. Electrostatic accelerators are limited in maximum energy by the physical ability to generate and manage high static voltage at high power levels. Electrostatic accelerators using Cockroft-Walton voltage multipliers are capable of energy levels of up to 1 MeV at high power levels, but the 10 MeV energy level utilized by many systems for effective irradiation is not typically available.

Cylindrical electron beam accelerators have been in use for a number of years. These accelerators generally operate by injecting electrons into a cylindrical cavity, where they are accelerated across the cavity by radio frequency energy pumped into the cylinder and redirected across the cavity by magnets to be further accelerated. Once the electrons reach a desired energy level, they are directed out of the cylinder toward a target.

RF linear accelerators have also generally been in use for many years and employ a series of cascaded microwave radio frequency tuned cavities. An electron source with direct current electrostatic acceleration injects electrons into the first of the cascaded tuned cavities. A very high energy radio frequency signal driven into the tuned cavities causes the electrons to be pulled into each tuned cavity by electromagnetic field attraction and boosted in velocity toward the exit of each tuned cavity. A series of such cascaded tuned cavities results in successive acceleration of electrons to velocities up to the 10 MeV level. The accelerated electrons are passed through a set of electromagnets that shape and direct the beam of electrons toward the target to be irradiated.

A typical industrial irradiation system employs an electron beam accelerator of one of the types described, a subsystem to shape and direct the electron beam toward the target and a conveyor system to move the material to be irradiated through the beam. The actual beam size and shape may vary, but a typical beam form is an elliptical shape having a height of approximately 30 millimeters (mm) and a width of approximately 45 mm. The beam is magnetically deflected vertically by application of an appropriate current in the scan deflection electromagnets to cause the beam to traverse a selected vertical region. As material to be irradiated is moved by conveyor through the beam, the entire volume of product is exposed to the beam. The power of the beam, the rate at which the beam is scanned and the rate that the conveyor moves the product through the beam determines the irradiation dosage. Electron beam irradiation at the 10 MeV energy level is typically effective for processing of food materials up to about 3.5 inches in thickness with two-sided exposure. Conversion of the electron beam to x-ray irradiation is relatively inefficient but is effective for materials up to 18 inches or more with two-sided exposure.

In addition to food materials, recent attacks on the United States Postal Service (USPS) have occurred in which highly dangerous *Bacillus anthracis* spores have been placed in envelopes and mailed, suggesting a need for irradiation of mail and related paper materials. The levels of radiation exposure that may be used to sanitize mail are significantly higher than those allowable for food. This is due to the fact that mail materials typically consist of paper and ink and are not intended to be consumed by individuals. The doses of radiation may therefore be set to relatively high levels that are effective in eliminating both spore forming bacteria such as *Bacillus anthracis* as well as viruses. Each of these types of pathogens are relatively resistant to ionizing radiation; spore forming bacteria because of the compactness and durability of the spores; and viruses due to the relatively small size of viral DNA molecules. The target dose established by the USPS is 56 kGy, which is 8 times higher than the maximum allowable dose for irradiation of frozen meat and 37 times higher than the typical dose applied to fresh ground beef for the elimination of *E. coli*. The considerations that must be accounted for in irradiating paper materials are somewhat different from those relating to irradiation of food materials, in large part due to the higher dose requirements and smaller cross sectional thickness of typical mail, but several concepts and configurations are applicable to both food and paper irradiation.

There are a number of prior art irradiation systems that utilize accelerators and conveying systems of some kind in a highly effective manner to irradiate articles and/or bulk material. Two such systems are described in U.S. application Ser. No. 09/685,799 filed Oct. 10, 2000 for "Irradiation System and Method" by S. Lyons, S. Koenck, B. Dalziel and J. Kewley and in U.S. application Ser. No. 09/795,058 filed Feb. 26, 2001 for "Bulk Material Irradiation System and Method" by S. Lyons, S. Koenck, B. Dalziel, D. White and J. Kewley, both of which have been incorporated by reference herein. Although irradiation systems such as these employ a number of useful features, additional features may be desirable for different types of irradiation applications. The present invention provides a number of features not previously known or described in the art, which are described in detail below.

BRIEF SUMMARY OF THE INVENTION

The present invention is an irradiation system that includes a conveying system for moving material to be irradiated through a processing area. An irradiation source applies radiation to material in the processing area. The conveying system is enclosed by a sealed conduit in at least the processing area, providing the capability to control the atmosphere inside the sealed conduit and to clean the interior of the sealed conduit according to industrial sanitation methods.

BRIEF DESCRIPTION OF THE DRAWINGS

FIG. 6A is a front section view illustrating an exemplary construction of the irradiation system shown in FIG. 3A.

DETAILED DESCRIPTION

Figure 1:
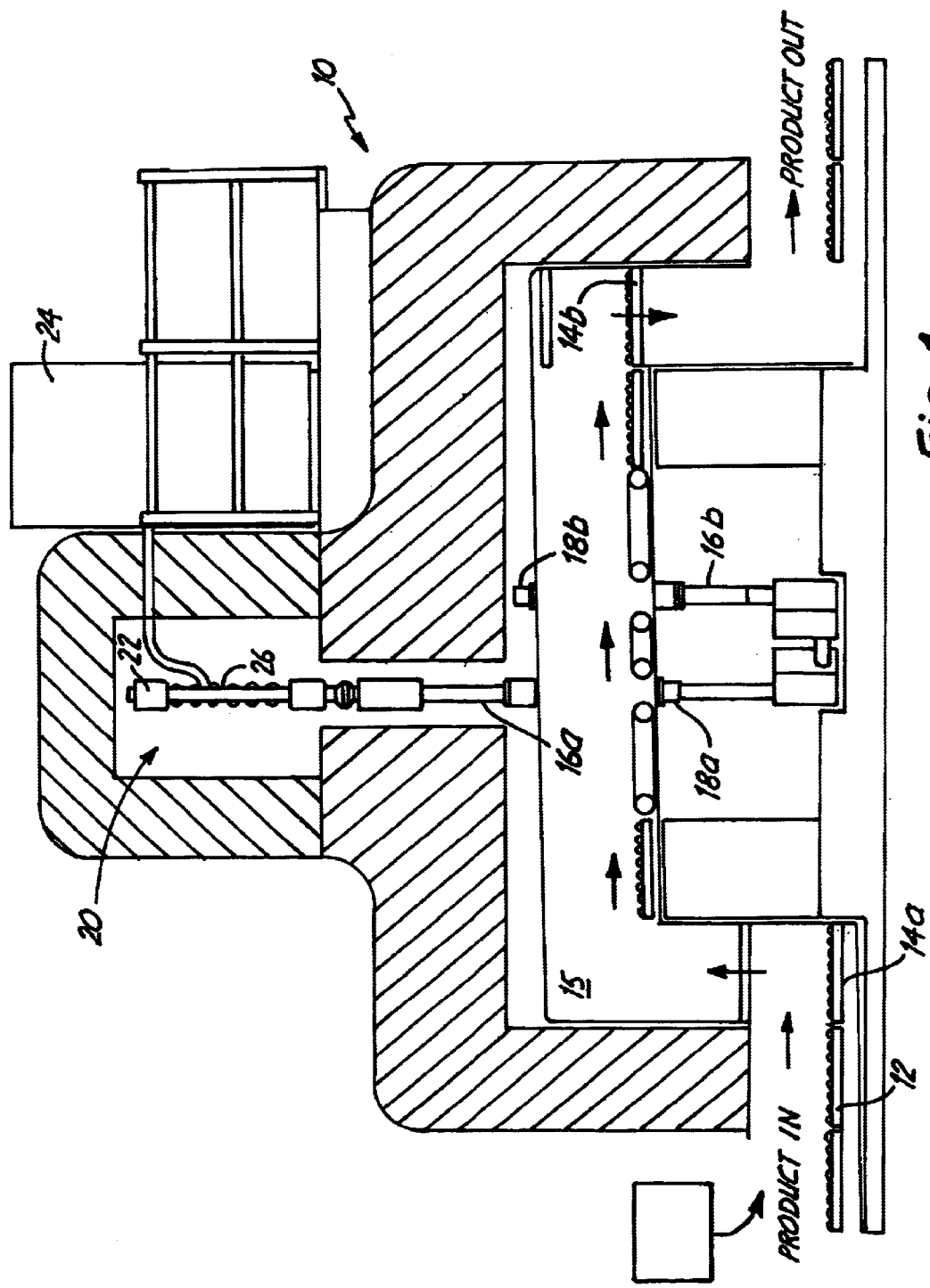
FIG. 1 is a front section view of an irradiation system in accordance with a first exemplary embodiment the present invention.

FIG. 1 is a front section view of irradiation system 10 according to an exemplary embodiment of the present invention. Irradiation system 10 includes product conveyor 12 and elevators 14*a* and 14*b* housed within sealed tube 15, scan horns 16*a* and 16*b*, optional dose monitors 18*a* and 18*b*, and accelerator 20 including electron gun 22, power supply 24 and accelerator waveguide structure 26. Product conveyor 12 is arranged to carry articles to be irradiated at a first elevation in an input portion of irradiation system 10, at a second elevation (due to elevator 14*a*) in a processing portion of irradiation system 10, and at a third elevation (due to elevator 14*b*) in an output portion of irradiation system 10. In the exemplary embodiment of FIG. 1, the first and third elevations are the same, but this does not necessarily have to be the case. Sealed tube 15 surrounds product conveyor 12 in all of the portions of irradiation system 10, which has a number of advantageous effects. The interior of sealed tube 15 may be cleaned and sanitized using conventional food processing industry practices including high pressure spray, antimicrobial foam and the like. An exemplary technique is generally referred to as a clean-in-place (CIP) industrial sanitation practice, which allows equipment operators to clean the interior of sealed tube 15 without disassembling irradiation system 10. This capability is particularly important because of the large and complex shield employed by the system. In addition, the interior of sealed tube 15 may be filled with a modified atmosphere such as nitrogen or carbon dioxide to exclude oxygen that may cause unwanted lipid oxidation effects during irradiation. The modified atmosphere is contained in the irradiation processing environment, so that a normal packaging environment and methodology can be used downstream from the irradiation area with virtually no modifications. One exemplary source of nitrogen for the modified atmosphere of irradiation system 10 is the nitrogen gas that is released when liquid nitrogen typically used for fast chillers evaporates. In such an embodiment, the nitrogen gas is directed to an input port of sealed tube 15 to displace the atmosphere therein and replace it with high nitrogen atmosphere having virtually no oxygen. The input port may be located near the input portion of sealed tube 15, or alternatively may be located internal to the system near the beginning of the processing portion. The shielding structure of irradiation system 10 has a very compact design, so that the amount of floor space required by the system is minimized.

In an exemplary embodiment, scan horns 16a and 16b, dose monitors 18a and 18b, and accelerator 20 are constructed and arranged in the manner generally described in U.S. application Ser. No. 09/685,799, which has been incorporated by reference herein. Accelerator 20 may employ an electron beam or x-ray radiation source, depending on the types of materials to be processed and the required penetration depths and processing rates.

In the exemplary embodiment shown in FIG. 1, items as large as 18 inches tall, 24 inches long and 24 inches wide may be carried through sealed tube 15 on product conveyor 12. Items to be irradiated may be placed in boxes or other types of shipping containers, or the items maybe individual unpackaged articles of some minimum size such as whole frozen turkeys, for example. In the case of individual items, the product conveyor may be constructed of a mesh belt or another carrier that provides a method of passing the items over lower scan horn 16b with appropriately designed radiation exposure.

Figure 2:
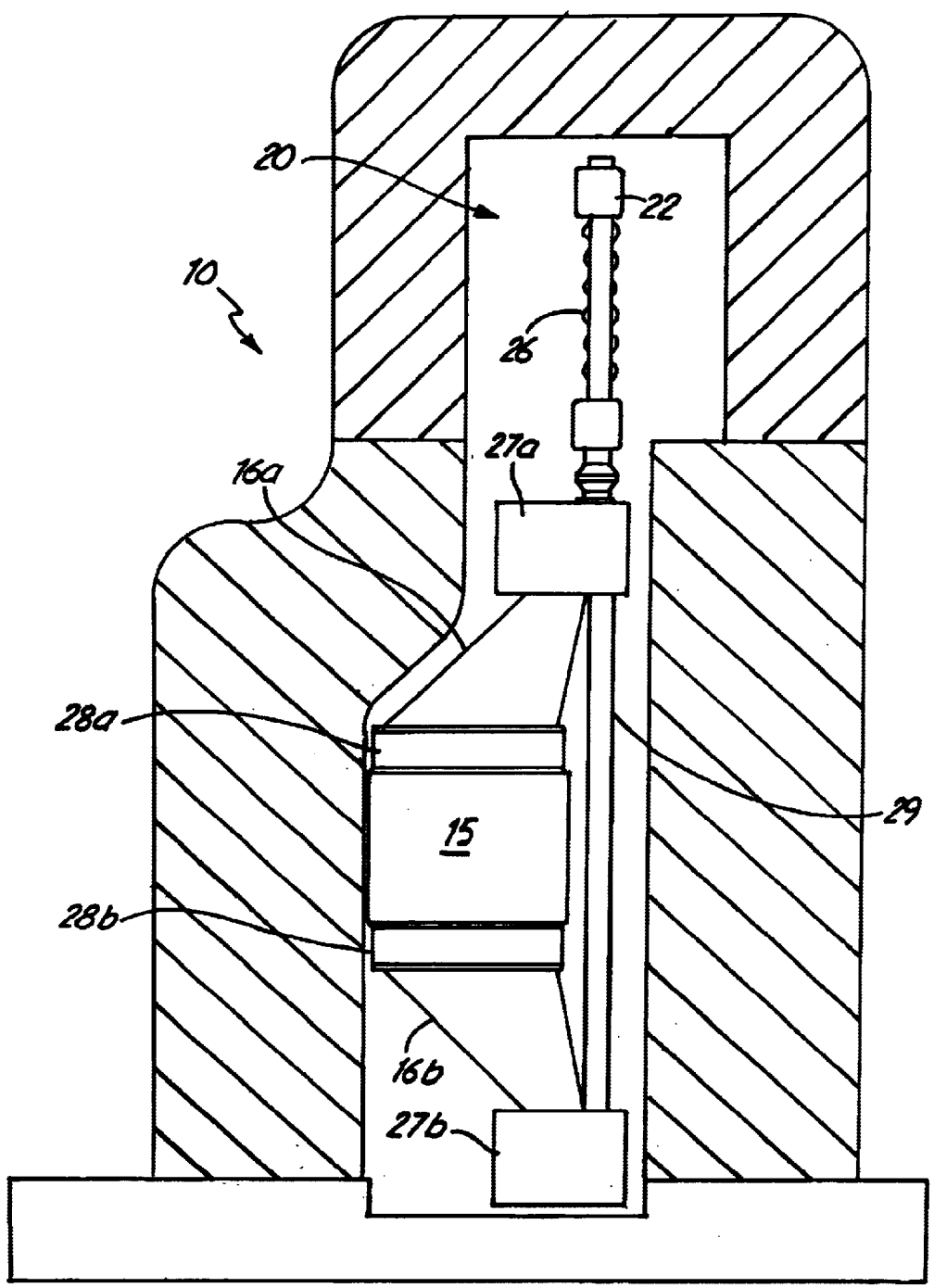
FIG. 2 is a side section view of the irradiation system shown in FIG. 1, with the section being taken through the processing portion of the system.

FIG. 2 is a side section view of irradiation system 10 shown in FIG. 1, with the section taken through the processing portion of the system. Product to be irradiated is carried through the system inside sealed tube 15. Electron gun 22 injects electrons into accelerator waveguide structure 26 which accelerates the electrons to upper quadrupole/deflection magnet assembly 27a and via path 29 to lower quadrupole/deflection magnet assembly 27b. Quadrupole/deflection magnet assemblies 27a and 27b operate under computer control to deflect the accelerated electrons in a scanning pattern, through scan horns 16a and 16b, respectively, and through respective optional beam straightener magnets 28a and 28b onto the product to be irradiated within sealed tube 15.

In an exemplary embodiment, sealed tube 15 has a wall with a thickness of approximately 0.125 inches or less, and is composed of a material generally recognized as safe (GRAS) for appropriate for contact with food. Exemplary materials are stainless steel, titanium, and other food contactable materials known to those skilled in the art. Radiation is directed into the interior of sealed tube 15 through a window area composed of a suitable radiation passing material such as a thin titanium foil, for example. In one embodiment, a single thin titanium foil serves as both the wall of sealed tube 15 in the window area and as the scan horn exit foil which isolates the vacuum environment of the scan horn from the outside environment and the environment in sealed tube 15. In another embodiment, a first thin titanium foil serves as the wall of sealed tube 15 in the window area and a second thin titanium foil serves as the scan horn exit foil to isolate the vacuum environment of the scan horn from the outside environment and the environment in sealed tube 15. In either case, the foil in the window area is designed to provide high physical strength, sufficient to withstand the pressures applied during industrial cleaning of the inside of sealed tube 15, while only minimally attenuating the radiation passing therethrough.

Figure 3A:
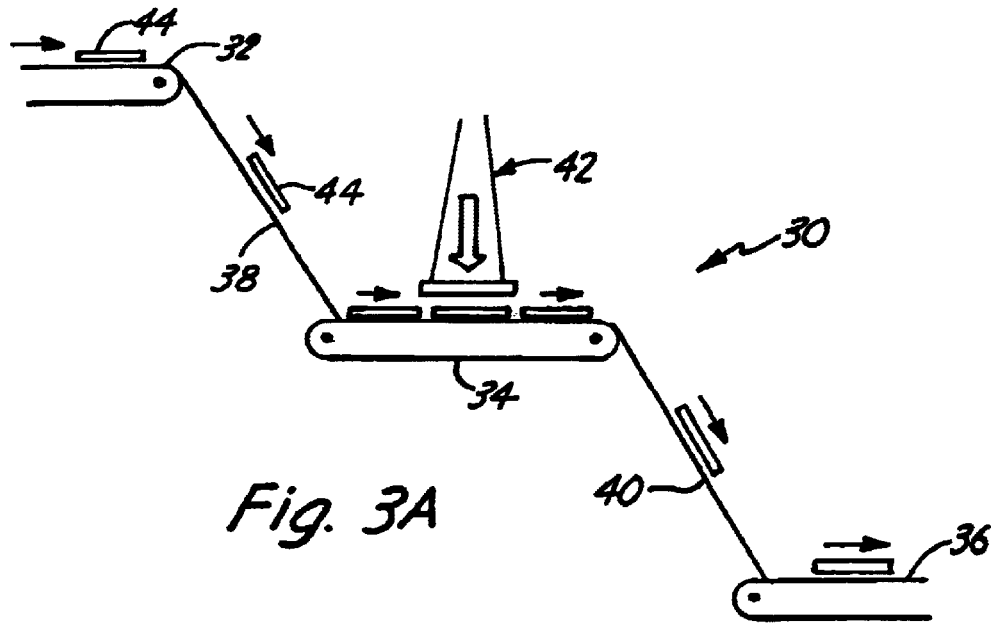
FIG. 3A is a schematic diagram of an irradiation system in accordance with a second exemplary embodiment of the present invention.

FIG. 3A is a schematic diagram of another exemplary irradiation system 30 in accordance with the principles of the present invention. Irradiation system 30 includes input conveyor 32, process conveyor 34 and output conveyor 36 at different elevations. Input conveyor 32 and process conveyor are connected by ramp 38, and process conveyor 34 and output conveyor 36 are connected by ramp 40. Irradiation source 42 is disposed to provide radiation to articles carried by process conveyor 34.

In operation, thin articles to be irradiated such as frozen ground beef patties 44 are carried by input conveyor 32 to ramp 38. For simplicity, the path of only a single patty 44 will be explained as it passes through irradiation system 30. Patty 44 slides down ramp 38 to process conveyor 34, which carries patty 44 past irradiation source 42 and on to ramp 40. Patty 44 then slides down ramp 40 to output conveyor 36, which carries patty 44 out of irradiation system 30, for further processing, packaging, storage or the like.

The slopes of ramps 38 and 40 are selected depending on the types of articles to be irradiated by the system. Frozen ground beef patties are generally solid and relatively frictionless, allowing the angle of ramps 38 and 40 to be shallow, such as between 30 and 45 degrees. Other food articles may be less inclined to slide freely down a sloping ramp, requiring the angle of the ramp to be more steep.

Figure 3B:
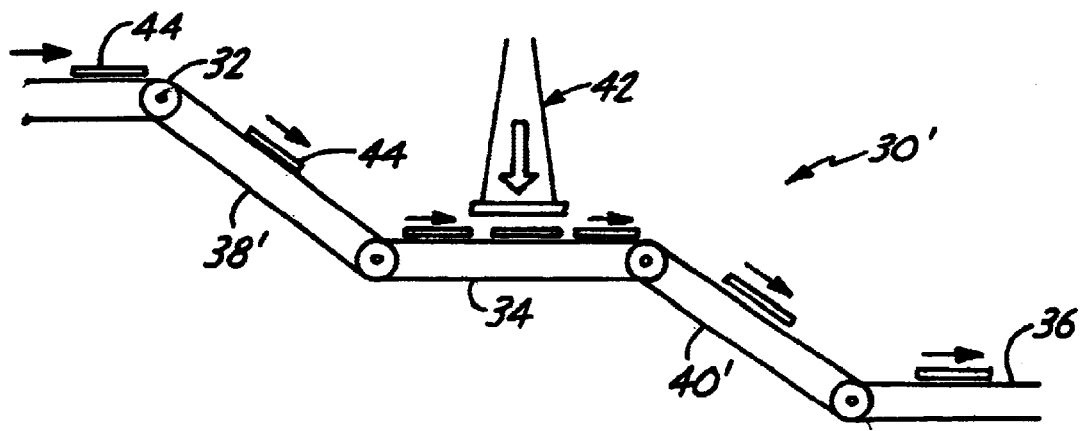
FIG. 3B is a schematic diagram of an irradiation system in accordance with a modified version of the second exemplary embodiment of the present invention.

FIG. 3B is a schematic diagram of irradiation system 30' in accordance with the principles of the present invention. Irradiation system 30' is similar to irradiation system 30 shown in FIG. 3A, except that ramps 38 and 40 are replaced by powered ramp conveyors 38' and 40'. Ramp conveyors 38' and 40' provide additional control of the speed of articles between input conveyor 32 and process conveyor 34, and between process conveyor 34 and output conveyor 36. Moreover, powered ramp conveyors 38' and 40' provide the capability to change the ramps from downward sloping to upward sloping in some embodiments, since mechanical power rather than gravity is used to change the elevation of the articles as they pass through irradiation system 30'.

Figure 4:
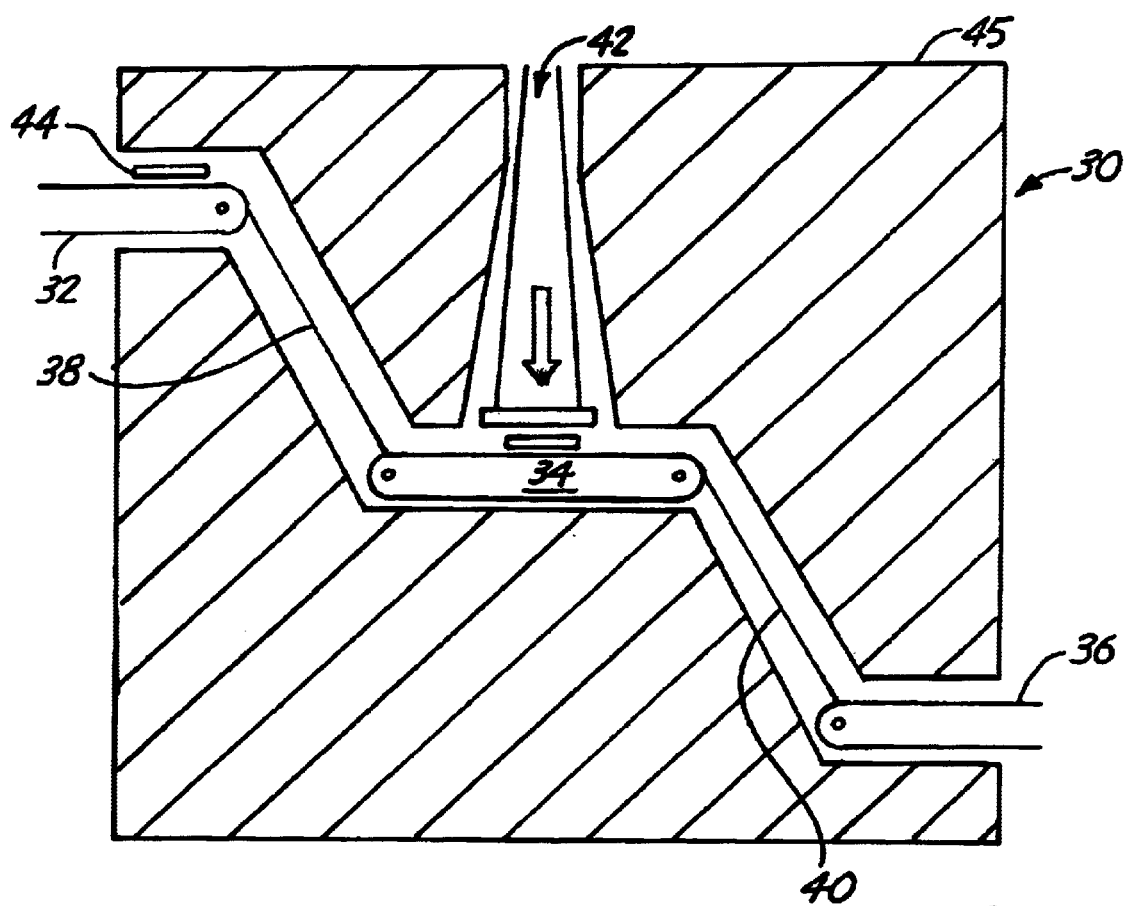
FIG. 4 is a schematic diagram of the irradiation system shown in FIG. 3A employing a surrounding radiation shielding structure.

FIG. 4 is a schematic diagram of irradiation system 30 employing surrounding radiation shielding structure 45. Shielding structure is constructed of suitable radiation absorbing material such as lead, steel, concrete or other appropriate material. Shield structure 45 is configured and arranged such that there is no straight line path for radiation to escape the shield containment structure surrounding the high intensity radiation exposure region under irradiation source 42.

The system of FIG. 4 could be utilized for processing food articles such as frozen ground beef patties, for example. However, it is also desirable for food handling systems to be readily compatible with food processing industry cleaning practices to meet sanitation requirements. The conveyors operating in a generally open environment surrounded by radiation shielding are not well suited for the aggressive cleaning that is presently used in the food processing industry.

Figure 5:
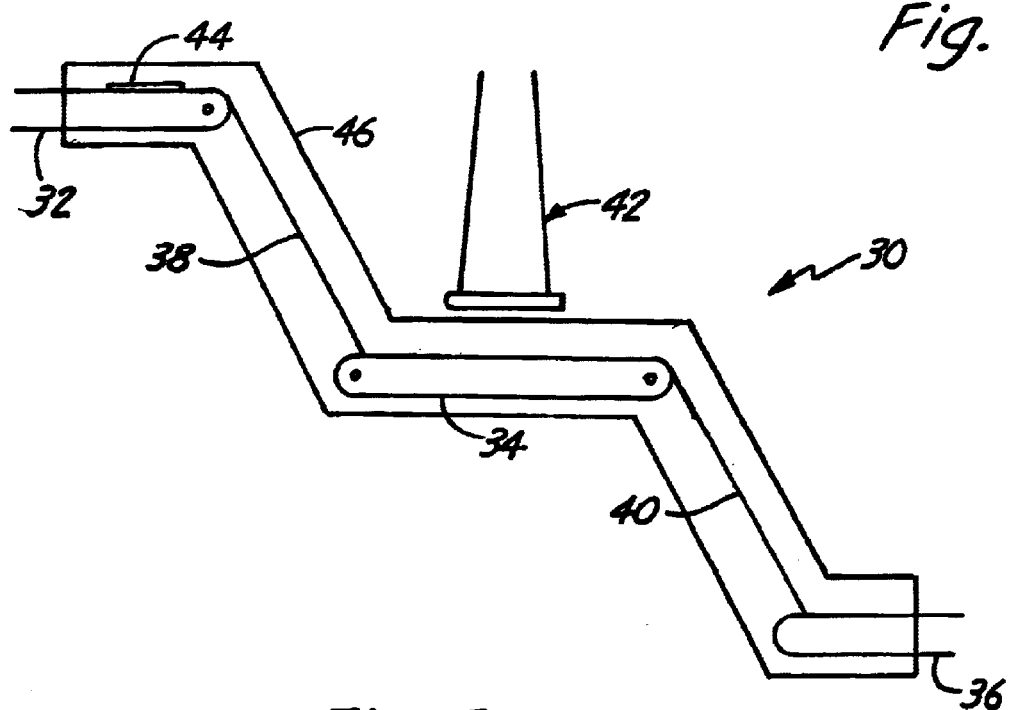
FIG. 5 is a schematic diagram of the irradiation system shown in FIG. 3A employing an enclosed material movement system.

FIG. 5 is a schematic diagram of irradiation system 30 employing an enclosed material movement system. The basic material movement is similar to that of FIGS. 3A, 3B and 4, however, the entire material movement system is enclosed within enclosed structure 46 consisting of relatively thin (e.g. 0.125 in. or less) stainless steel, as described above with respect FIGS. 1 and 2. Enclosed structure 46 is liquid tight and completely surrounds and contains the food handling conveyors and downward sloping chutes. Radiation may be directed to the interior of enclosing structure 46 by providing a window area below the radiation source consisting of suitable radiation passing material such as a thin titanium foil. The interior of enclosed structure 46 may be cleaned and sanitized using normal food processing industry practices including high pressure spray, antimicrobial foam and the like. A shield structure similar to the type illustrated in FIG. 4 may surround enclosed structure 46 to provide the radiation shielding necessary for safe operation of the system.

Figure 6B:
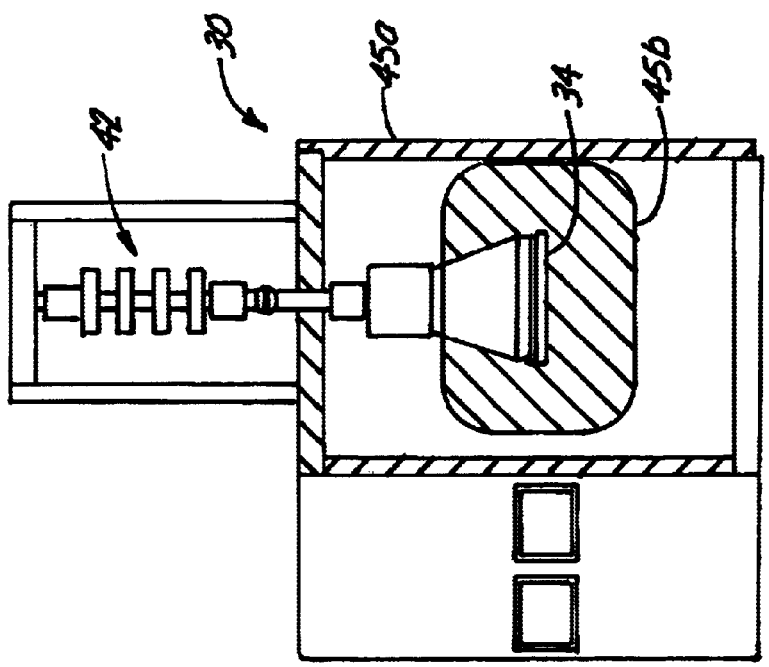
FIG. 6B is a side section view taken at the radiation beam line illustrating an exemplary construction of the irradiation system shown in FIG. 3A.

FIG. 6A is a front section view, and FIG. 6B is a side section view taken at the radiation beam line, illustrating an exemplary construction of irradiation system 30. Uniformly formed, solid articles such as frozen ground beef patty 44 may be handled by moving the articles via input conveyor 32 to downward sloping ramp 38 that allows the articles to be stacked against each other on edge, and held in place vertically by the thickness of the channel inside enclosing structure 46. Gravity will cause the food articles to move downward until process conveyor 34 moves the lowest article off of ramp 38 for movement under irradiation source 42. In general, it is anticipated that the movement rate of food articles such as ground beef patty 44 will be uniform and sufficiently spaced that stackup of the articles at the end of ramp 38 will not be experienced, however, the structure of ramp 38 and enclosing structure 46 does have the potential to provide a buffering or queuing utility if the instantaneous rates of material movement on input conveyor 32 and process conveyor 34 are somewhat different. In general, the rates of the conveyors will be the same and the control of the rates will be coordinated with the processing equipment that prepares the food articles for irradiation processing.

An alternate system configuration (not shown) corresponding generally to the structure of FIGS. 6A and 6B could be constructed to irradiate loose bulk material to be processed such as grain, palletized materials such as dry pet food or other loose bulk materials. In this type of system, the input chute would be constructed to contain a selected amount of bulk product to be processed. The output of this chute would be a structure that would form the bulk material onto the processing conveyor at a predetermined appropriate thickness for irradiation processing. For example, if the material to be processed is loose bulk grain such as wheat, the thickness of the wheat on the process conveyor may be chosen to be 1.0 inches for processing with a single sided 4.7 MeV accelerator. Movement and processing of loose bulk material of such type would require a conveyor belt and material movement system that could be placed within an enclosing structure as described without malfunctioning due to the buildup of residual material within the enclosing structure.

As is illustrated in FIGS. 6A and 6B, the shielding structure is large due to the typical radiation attenuation requirements for safety of operating personnel. Even so, the structure is small compared to the size of a facility that would be required to place a high intensity radiation generating device within. The physical floor space required for the system is further reduced by using vertically disposed components such as the electron beam accelerator and its associated drive electronics. FIGS. 6A and 6B also illustrate that process conveyor 34 with enclosing structure 46 may be accessed relatively easily by removing outer shield wall 45a and/or inner shield wall 45b and sliding the conveyor assembly out the end. In one exemplary embodiment, door structures 47a and 47b are provided in outer shield wall 45a to allow easy access to interior parts such as process conveyor 34. By allowing the shield walls to be opened, the entire internal process conveyor section including enclosing structure 46 may be removed by sliding it out of the straight cavity located inside the shield structure.

If in the process of moving food articles through the conveyor assembly, a food article should get stuck, broken, jammed or otherwise lodged inside the conveyor assembly, the blockage in the conveyor assembly may be removed and the system returned quickly to operation by opening the shield walls to provide ready access to the material movement path. A variety of cleaning tools may be used to push the blockage out either end of the material movement path that are shaped and sized to fit the path dimensions. If none of these methods are successful, the blockage may be removed by removing the entire process conveyor assembly with enclosing structure and flushing it out with high pressure, high temperature cleaning water. This cleanout may be done in a different location so that the food processing room need not be taken down for extended cleaning.

Nitrogen or other modified atmosphere for irradiation exposure may be provided with the irradiation system previously shown and described by introducing the modified atmosphere gas into the enclosing structure to displace the naturally occurring atmosphere that the food articles are normally surrounded with. The modified atmosphere may be introduced at the input of the enclosing structure near the beginning of the input chute, or it may be introduced internal to the system near the beginning of the process conveyor to force positive pressure of the modified atmosphere gas at the interior of the system. The objective is to displace the normal atmosphere during the actual irradiation processing to minimize oxidation effects. Once the processing is completed, the atmosphere is not critical until final packaging, which may have its own criteria such as high oxygen modified atmosphere, for example.

In one exemplary embodiment, "air curtains" are formed outside of the processing area of the irradiation system, such as at entrance and exit points of the system. The air curtains maintain a slight positive nitrogen pressure inside the sealed conduit enclosing the conveyor, helping to ensure that oxygen is properly excluded from the processing area. Alternatively, oxygen can be excluded completely by sealing the entire irradiation system and modifying the atmosphere therein.

Until the food material has been placed in its final packaging, it is important to isolate the processed but unpackaged material from potential external contamination. In an exemplary system employing the present invention, an enclosing structure is disposed to surround a conveyor that moves processed food articles to final packaging equipment.

Figure 7:
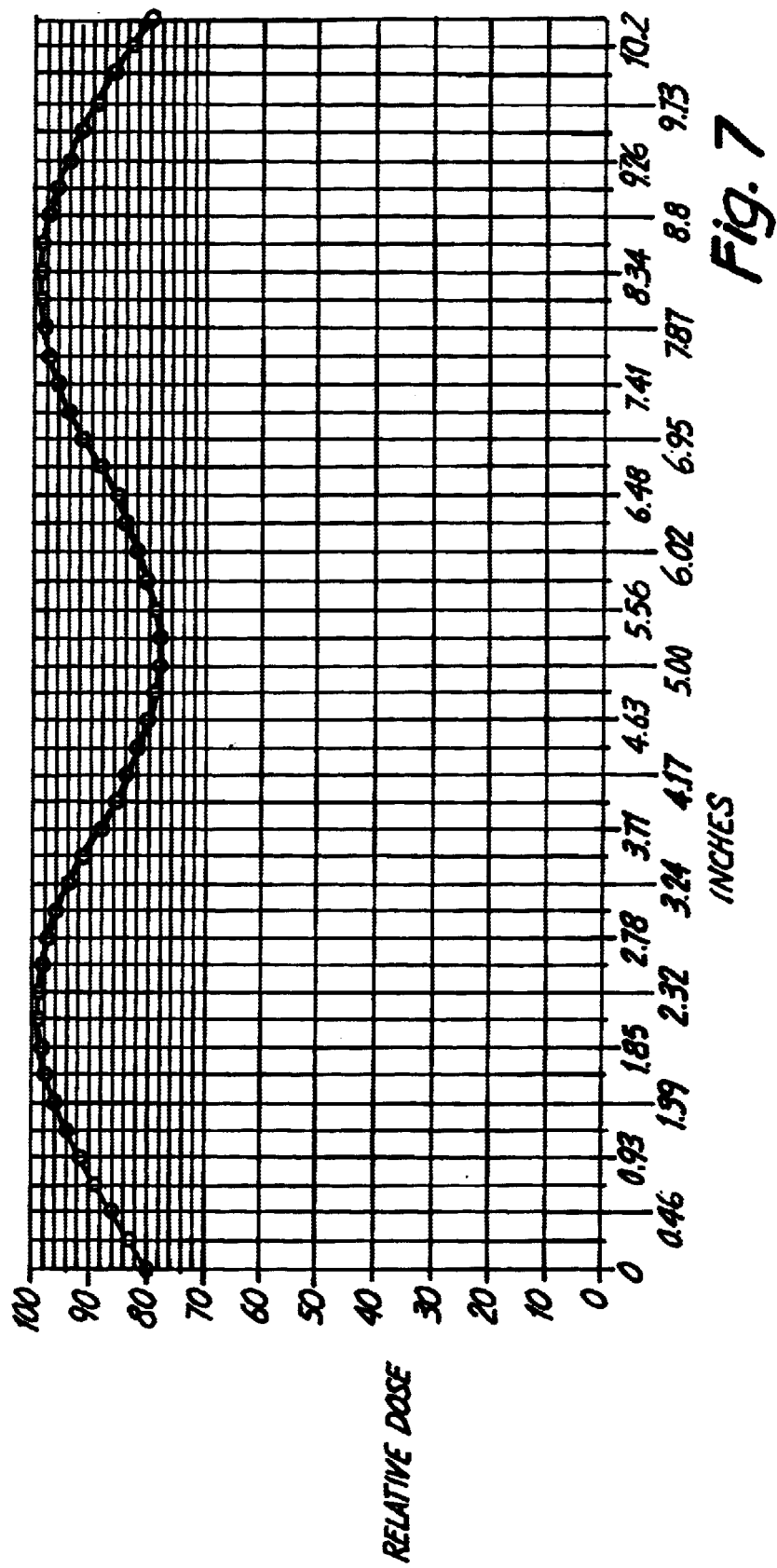
FIG. 7 is a graph illustrating a representative depth-dose curve for 10 MeV radiation applied to both sides of materials of 34% water equivalent density.

One particular application of irradiation technology is the sanitization of mail or other paper products. The primary differences between irradiation of food products and paper products are the densities of the materials and the allowable radiation dose. In general, electron beam irradiation systems are designed at various power and energy levels, with the maximum allowable energy established by the FDA and USDA at 10 MeV. This level has been selected as an upper bound due to the fact that no materials are activated and rendered radioactive by exposures at or below this level. While useful irradiation processing may be performed with electron beam energies as low as 1 MeV, the penetration depth that is possible at such energies is less than 0.3 inches for water equivalent density articles and is therefore limited in application. An electron beam with energy of 10 MeV, however, is capable of penetrating water equivalent density articles with thickness up to about 1.5 inches with good dose uniformity. Two-sided electron beam exposure is appropriate for water equivalent density applications up to 3.5 inches thick. Mail materials range in density from 26% to 34% of water density, which has the effect of multiplying the potential thickness that may be processed. In the worst case (maximum density), the potential thickness of mail material that may be processed by two-sided 10 MeV electron beams is 3.5/0.34=10.3 inches. If the density of the mail material is at the low end of the range, the maximum thickness may be as high as 3.5/0.26=13.5 inches. Thus, a practical maximum thickness for mail material processing is 10.3 inches. FIG. 7 is a graph illustrating a representative depth-dose curve for 10 MeV radiation applied to both sides of materials of 34% water equivalent density.

Irradiation of mail articles may be performed in a number of configurations depending on the type of mail and how it is packaged and received. In general, mail is received into a post office either from local or distant sites. The distant sites typically ship mail by truck or air and in either case the mail material is received at a shipping dock after being unloaded from a truck. Mail received from local sites may come in several configurations. Loose mail may be picked up by a letter carrier or from collection points such as the familiar "blue boxes" that are located on street corners or near busy locations. Businesses may prepare bulk mail in presorted mail trays provided by the USPS.

An important consideration for any type of mail as it is received into a local post office is to protect postal workers wherever they may be exposed to dangerous pathogens, and to locate the pathogen reducing sterilization step as early in the process flow as possible to minimize the risk of exposure. To provide this comprehensive protection to postal workers as well as to protect citizens well downstream from the postal environment, a systematic method of containing and reducing pathogens should be employed. This system should include:

Containing pathogens in postal material at the initial points of induction into the system. These points include collection points, "blue boxes" and individual residential mail boxes.

Transporting the postal material to the post office without allowing release of harmful pathogens that may expose the postal worker.

Eliminating harmful pathogens before removing the postal material from its containing environment.

Presently, letter carriers and collection point drivers collect postal material in loose form without sorting and with minimal orientation and stacking. Reusable plastic tubs are used to transport loose postal material from the collection point to be dumped into a cart placed in the back of the postal pickup vehicle. Letter carriers typically carry a shoulder bag to transport letters to be delivered to and picked up from residences. Outgoing mail is similarly placed in a cart or tub in the postal vehicle. A substantial amount of loose local mail is received into the post office facility and is handled in bulk form. Typically, hoppers, conveyors and various types of sorting equipment are used to handle this loose mail. When the loose mail is properly sorted and processed, it is typically placed in one of a variety of handling trays for outgoing shipping to remote sites.

It is possible that contaminated mail material may be placed into the postal system by either being deposited into a collection point or by being placed in outgoing mail from a residence. If this occurs, the letter carrier may be potentially exposed to the contaminating pathogen, and in the case of *bacillus anthracis* is most vulnerable in closed spaces with circulating air such as in a closed vehicle. This threat may be mitigated by replacing the plastic tub carrier that is typically placed in the bottom of the collection point with a specially configured sealable bag. This bag may be constructed of a tough, flexible plastic or rubber material with a continuous zipper structure of the type used in underwater gear to provide a water tight seal. When the zipper is closed, air that is trapped inside the bag may be released by providing a filtering vent. The vent may be constructed with a very fine replaceable filter such as the 0.3 micron type used by workers who may be exposed to airborne pathogens. The bag may be held in place inside the collection point by an internal collapsing metal or plastic frame, or it may be hooked in place by hooks inside the collection box that protrude through corresponding grommets in the bag. The objective is for the bag to be zipped shut by the carrier before airborne pathogens may be diffused into the air. Once the bag is zipped shut, the trapped air may escape slowly through the filtering vent until there is virtually none remaining. This has the benefit of allowing the bag to occupy the minimum physical volume inside the postal vehicle for maximum efficiency.

Postal material collected from residences may be similarly safeguarded by providing the letter carrier with a smaller version of the same type of containing bag. The residential collection bag may be flat in shape with a zipper along an edge and a filtering vent to allow trapped air to escape. When the bag is full, it may simply be placed inside the larger bag or it may be placed in the ordinary flat tub box that is presently being used.

When the sealed bags are returned to a post office for processing, it would clearly be hazardous for personnel to open them if they should contain harmful pathogens. Exposing the entire unopened bag to radiation to eliminate the pathogens inside will mitigate this threat.

Mail received from remote sites by truck or air is typically received at a shipping dock by truck delivery. The trucks may contain mail packaged in several forms including standard 40"×48" pallets loaded with stacks of mail trays, large carts containing loose mail and carts containing a mixture of loose mail and mail trays. It must be assumed that the status of the incoming mail is generally unknown and may contain harmful pathogens. These harmful pathogens may be eliminated by irradiating the entire shipping unit, which requires a radiation source capable of penetrating up to 40 inches or more. The two potential deep penetrating radiation source candidates are gamma sources such as Cobalt 60 and machine generated x-rays. Each of these radiation sources has significant disadvantages that make them relatively undesirable for applications in post offices. Cobalt 60 is a radioactive isotope that must be handled with care and constantly produces radiation. X-ray radiation may be turned off when not in use, but is quite inefficient and costly to generate due to the low conversion efficiency from electron beam accelerator to x-ray which requires a massive electron beam accelerator to create useful x-ray capacity. Electron beam radiation is by far the most efficient to generate, but is capable of penetrating only to about 10.3 inches of thickness as illustrated by FIG. 7.

The optimal solution to this problem is to break the remote shipping units down to a size that may be handled and processed by an electron beam sanitizing system. Since the remotely shipped mail material may be packaged in either loose form or in mail trays, it is necessary to process the mail material in either form. While this could be accomplished by utilizing two separate processing systems, this would be inefficient and costly, especially in smaller post offices. A single electron beam irradiation system for applying radiation to both loose material and mail packaged in trays according to the principles of the present invention is described below.

Figure 8:
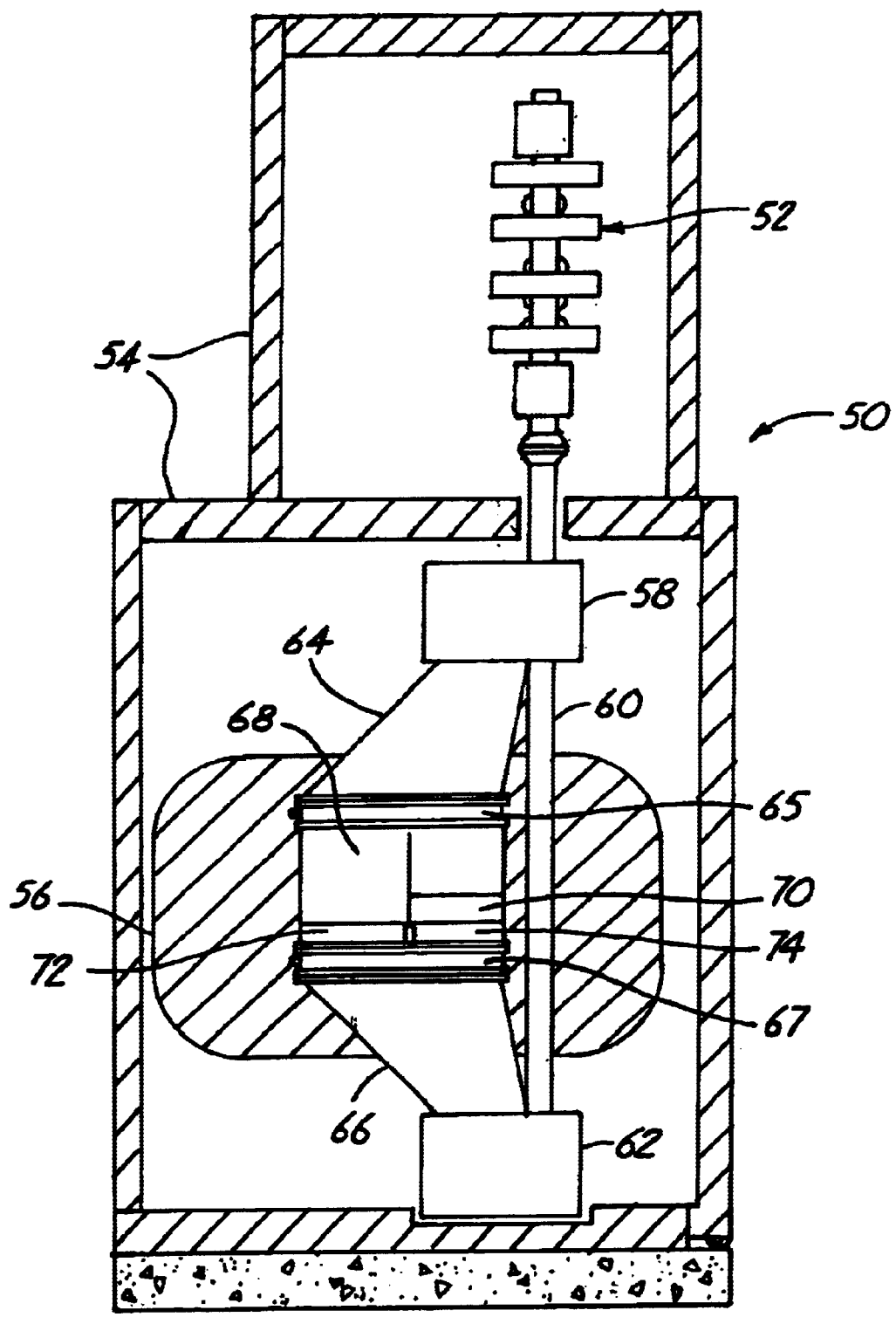
FIG. 8 is a cross-section view of a mail sanitizing system according to a third exemplary embodiment of the present invention.

FIG. 8 is a cross sectional view of mail sanitizing system 50 according to an exemplary embodiment of the present invention. Mail sanitizing system 50 includes linear accelerator 52, external shield enclosure 54 and internal shield enclosure 56. Linear accelerator 52 is operable to generate high velocity electrons that are directed downward toward upper bending and beam forming magnet assembly 58, and through pathway 60 to lower bending and beam forming magnet assembly 62. After passing through magnet assemblies 58 and 62, the electron beam is spread out and directed through upper scan horn 64 and lower scan horn 66 (and through respective optional beam straightening magnets 65 and 67), for direction toward the material to be irradiated. The electron beam is generated in the form of short pulses by a very high power radio frequency (RF) source (not shown) that drives the linear accelerator in a manner well known to those of ordinary skill in the art. A computer system is coupled to an amplifier subsystem to drive upper magnet assembly 58 and lower magnet assembly 62 to control the path of the electron beam toward the target.

Processing region 68 between scan horns 64 and 66 is approximately 15 inches tall and 15 inches wide, and may contain material up to about 10.3 inches thick to be processed by the electron beam. To appropriately expose material this thick, it is necessary to expose the material from two opposite sides. This double-sided exposure is accomplished by sequentially stepping the electron beam across both sides of processing region 68 under computer control so that full exposure from each side is achieved. Alternatively, a system employing two irradiation sources could be used at greater expense.

Processing region 70 is approximately 4 inches thick and may be exposed sufficiently by radiation from one side only. This is accomplished by stepping the position of the electron beam under computer control across the top side of processing region 70 only. Thus, the electron beam is controlled by the computer to sequentially step across the top sides of processing regions 68 and 70 and across the bottom side of processing region 68. In an exemplary embodiment, processing regions 68 and 70 are contained within a sealed conduit formed of relatively thin stainless steel or another appropriate material.

Material to be processed is transported on roller conveyor 72 and belt conveyor 74 beneath processing regions 68 and 70, respectively. Roller conveyor 72 is not continuous, but has an aperture through which lower scan horn 66 directs the electron beam toward processing region 68 from the bottom side. Belt conveyor 74 is continuous, since no electrons are directed toward processing region 70 from the bottom side and since it will typically be carrying loose material.

Figure 9:
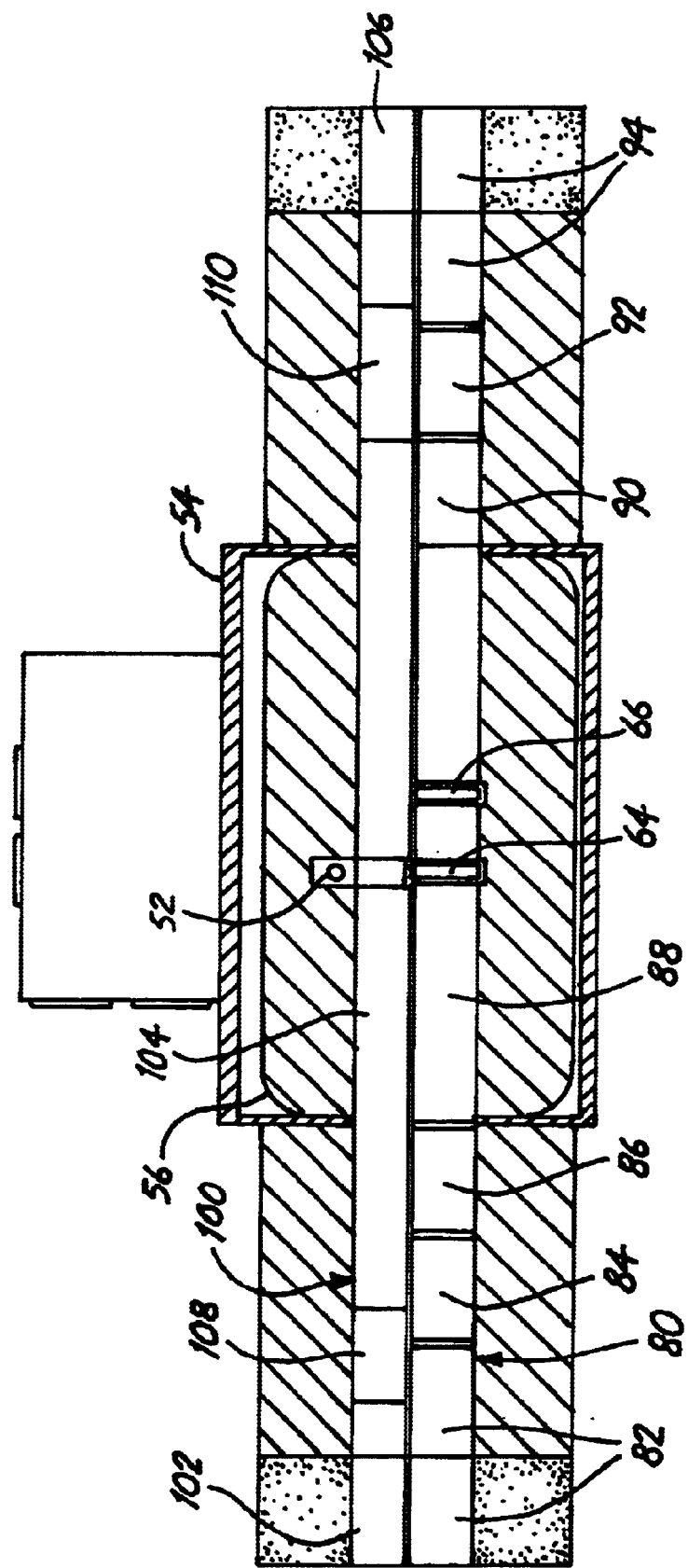
FIG. 9 is a top section view of the mail sanitizing system shown in FIG. 8.

FIG. 9 is a top section view of mail sanitizing system 50 shown in FIG. 8. Two independent side-by-side conveyor paths are provided for loose mail and for mail carried in trays. Internal shield 56 accomplishes the majority of the radiation attenuation, while external shield 54 reduces the lower intensity backscatter radiation that may be produced by the various beam manipulation components such as the magnets and scan horns. Modular end shield structures 76 and 78 provide the shielding at the ends of the conveyor path through internal shield 56. Modular end shield structures 76 and 78 may be configured in a number of different ways to shield the entry and exit paths of mail sanitizing system 50, depending on the type of material that is being handled.

Tray path 80 uses powered entry rollers 82 to roll trays or sealed bags onto lift elevator 84. Elevator 84 raises the level of the tray or bag, and powered rollers on elevator 84 convey the item on to elevator queue roller 86, which subsequently rolls the item onto process conveyor 88. The item passes on to outbound elevator queue conveyor 90, where it is rolled onto outbound elevator 92 which receives the item and lowers it to the level of exit rollers 94.

Loose mail path 100 uses continuous ramp conveyors including entry conveyor 102, full length process conveyor 104 and exit conveyor 106. Entry conveyor 102 is coupled to process conveyor 104 by entry chute 108, and process conveyor 104 is coupled to exit conveyor 106 by exit chute 110.

Figure 10:
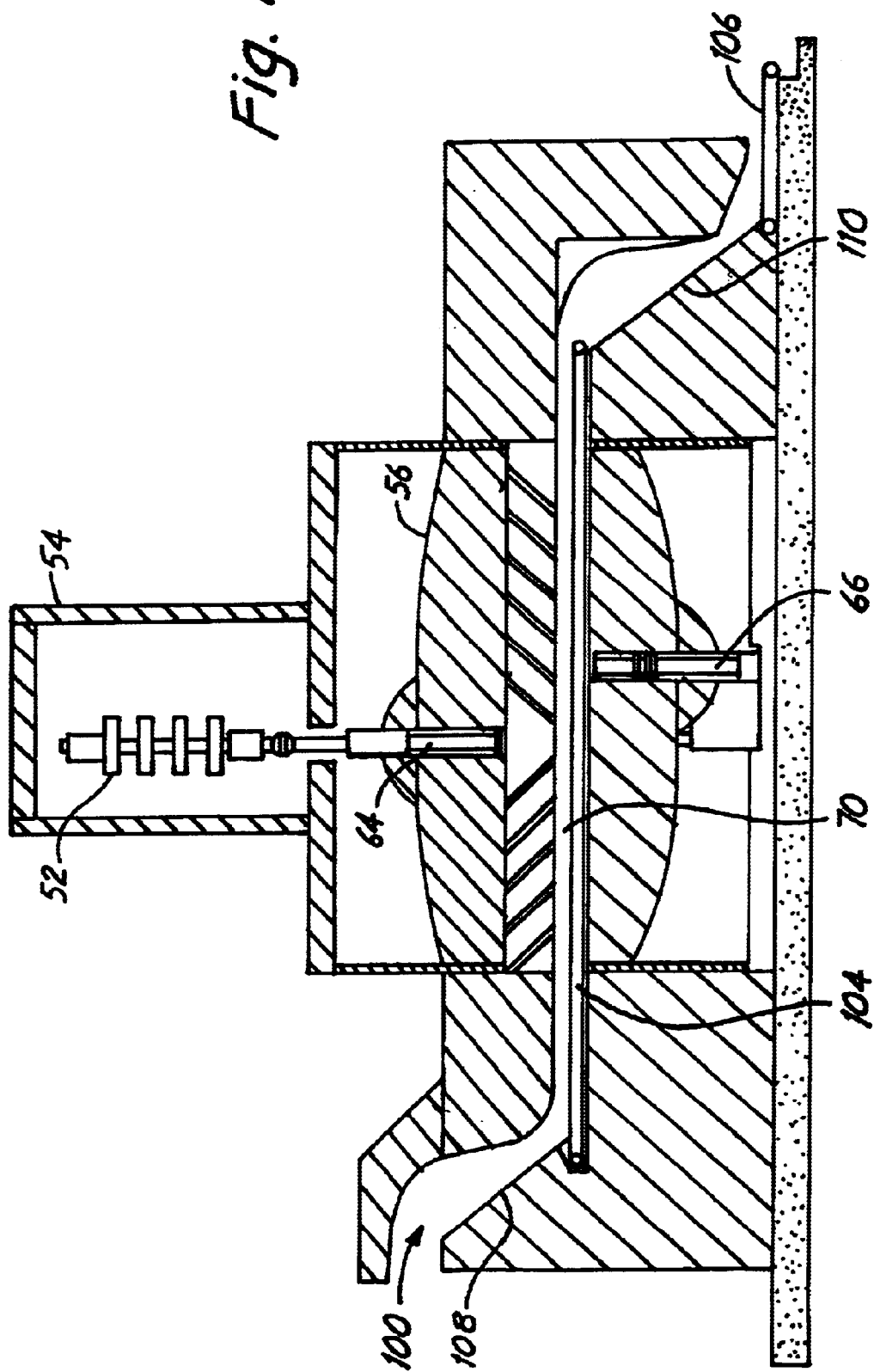
FIG. 10 is a front section view of the mail sanitizing system shown in FIGS. 8 and 9, with the section being taken through the loose mail path of the system.

FIG. 10 is a front section view of mail sanitizing system 50 shown in FIGS. 8 and 9, with the section being taken through loose mail path 100. Entry conveyor 102 (FIG. 9) moves loose mail to entry chute 108, where it slides down onto process conveyor 104. Process conveyor 104 carries the loose mail past the irradiation exposure region to exit chute 110, where it slides down onto exit conveyor 106 to be carried out of the system.

Figure 11:
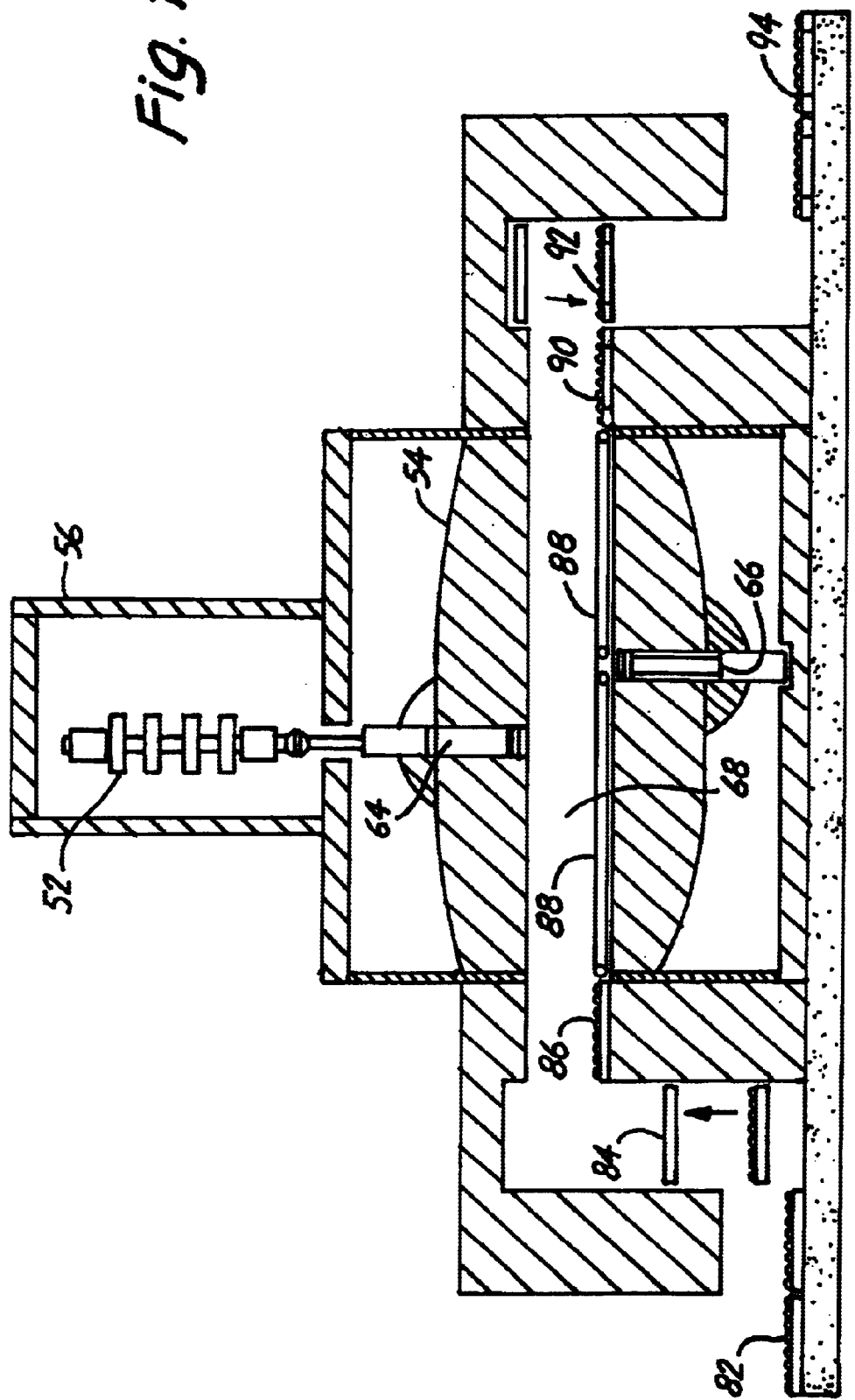
FIG. 11 is a front section view of the mail sanitizing system shown in FIGS. 8 and 9, with the section being taken through the tray path of the system.

FIG. 11 is a front section view of mail sanitizing system 50 shown in FIGS. 8 and 9, with the section being taken through tray path 80. Trays or bags of mail are placed on powered entry rollers 82, where they are moved onto entry lift elevator 84 and up to the level of elevator queue roller 86. The trays or bags are then moved onto process conveyor 88 when the controller determines that the previous item has moved down process conveyor far enough that the items will not collide with one another and potentially upset the steady flow of items being passed through the irradiation area. Process conveyor 88 includes a gap to allow unimpeded irradiation from the bottom side of the item through lower scan horn 66. The item then moves off of process conveyor 88 onto outbound elevator queue conveyor 90, and then to outbound elevator 92 which lowers the item down to the level of exit rollers 94.

The nominal speed of the items through mail sanitizing system 50 is dependent on the applied dose and the power of linear accelerator 52. For a typical 15 kW accelerator processing trays of nominally 15 inches width, the conveyor may be moving at a speed of approximately 0.5 inches per second or 30 inches per minute in an exemplary embodiment. Postal boxes and trays are typically approximately 24 inches long, so each tray would take approximately 48 seconds to process. This tray processing time determines the speed that the elevators must cycle and be in position to receive the next tray or bag coming into or out of the system. In general, the elevators will cycle much faster than 48 seconds and the entry, queue and exit rollers can move much faster than 0.5 inches per second to move items into and out of the system for processing.

As shown in FIGS. 8–11, the travel path through internal shield 56 for both trays and loose mail is a straight rectangular shaft that receives conveyor assemblies that are inserted from the end of internal shield 56. Each of the conveyor assemblies may be independent of one another and may be "mixed and matched" to meet particular handling requirements. For example, if a relatively small post office expects to need to process a roughly equivalent amount of loose and packaged mail, it may specify a system configuration that includes one loose and one package conveyor assembly. If the post office is substantially larger, it may wish to have additional loose mail capacity, in which case an additional system with two loose mail conveyors may be configured. Conversely, if additional packaged mail processing capacity is needed, an additional system with two elevator/conveyor paths may be configured.

The width and height of tray path 80 may be modified to most efficiently accommodate packaged materials including trays or bags. Reducing the height of the straight rectangular path through internal shield 56 generally improves the shielding characteristics and eases the shielding requirements for the end shield structures. In some embodiment, it is possible to replace the two single "half-conveyors" with a single conveyor path that is the full width of the straight rectangular path through the internal shield. This would allow processing of items as large as 24 by 30 inches by up to 15 inches. The end shield structure for a system configuration of this type would include a larger (wider) elevator to lift the large items up to the queue rollers for movement onto the process conveyor.

Since tray path 80 and loose mail path 100 consist of a conveyor or rollers located within an enclosing structure, it is possible to control the atmosphere inside the enclosing structure if necessary. This is of critical importance for processing of food materials that may be degraded by exposure to ionizing radiation in the presence of oxygen. Non-food items such as postal material are generally not subject to the same considerations as food materials, although it has been observed that irradiation of postal materials at high doses can result in the production of carbon monoxide or other gases that could potentially be harmful to personnel. It is therefore beneficial to have the ability to control the atmosphere even for irradiation of postal material. Reduction of carbon monoxide or ozone production can be accomplished by excluding ambient oxygen from the immediate area of the electron beam exposure. Gases such as nitrogen or carbon dioxide could be used for this purpose. It is presently assumed that the specified doses applied to postal material will not result in significant self-heating. It is possible, however, that certain items or materials placed in the mail might absorb an inordinate amount of energy and get hot enough to burn. This potentially dangerous condition could also be mitigated by excluding ambient oxygen from the internal volume of the conveyor shaft structure. Evaporated liquid nitrogen is well suited for this application due to its relatively low cost and its beneficial cooling characteristics for removing heat from system components that must be thermally managed.

The capacity of mail sanitizing system 50 is determined primarily by the power of linear accelerator 52 that generates the electron beam radiation source. It is generally uneconomical to fabricate a linear accelerator of higher power than about 15 kW. It is possible, however, to configure a system with two or more 15 kW accelerators to increase processing capacity. This is also economically advantageous, since the expense of shielding and material handling components may be shared. A further advantage of constructing a system with two or more accelerators is that there is built-in redundancy that would allow the system to continue operating even in the event of a failure of one of the accelerator subsystems. This embodiment with partial failure would have reduced processing capacity, but this would in most cases be preferable to complete system unavailability.

Although the embodiments shown in FIGS. 8–11 have been described with respect to irradiation of mail and other paper articles, it should be understood that many of the principles of those embodiments are also applicable to other materials, such as many types of food articles for example. The embodiments of the invention described above are highly effective and efficient for irradiation of mail and other paper materials, and also for irradiation of food articles such as ground beef. Ground beef is typically packaged in modified atmosphere packaging (MAP) with either very high or very low oxygen concentrations. High oxygen MAP has become the preferred MAP technology for case-ready fresh meat packaging. Since irradiation in high oxygen environments leads to the generation of ozone and causes oxidation of lipids that can result in unpleasant odors and tastes, irradiation of ground beef must be performed prior to completion of the high oxygen packaging, preferably in an in-line process.

There are two basic types of high oxygen MAP material handling systems that are characterized as either using pre-formed or thermoformed material trays. MAP systems that use pre-formed trays operate by removing each individual tray from a stack and filling it with material on a continuously moving conveyor. The trays may be conveyed from the material filling station to an irradiation system as described above that has a continuously moving conveyor as well. The irradiation system applies radiation in a sequence of overlapping circular or elliptical spots to create a relatively uniform radiation dose. The lateral magnetic deflection of the radiation beam and the longitudinal movement of the material on the continuously moving conveyor provide the area coverage of the material. Thus, the embodiments previously described are quite effective for irradiation of materials in a pre-formed tray packaging system.

Thermoformed material trays require a rather different material movement methodology. Thermoforming generally involves a process of applying heat to plastic materials that soften at high temperatures and may be formed to desired shapes. Thermoforming packaging systems typically form material trays by mechanically gripping a sheet of thermoplastic material with an accurately registered chain and feeding it into a forming system consisting of a heating station followed by a forming station.

Figure 12:
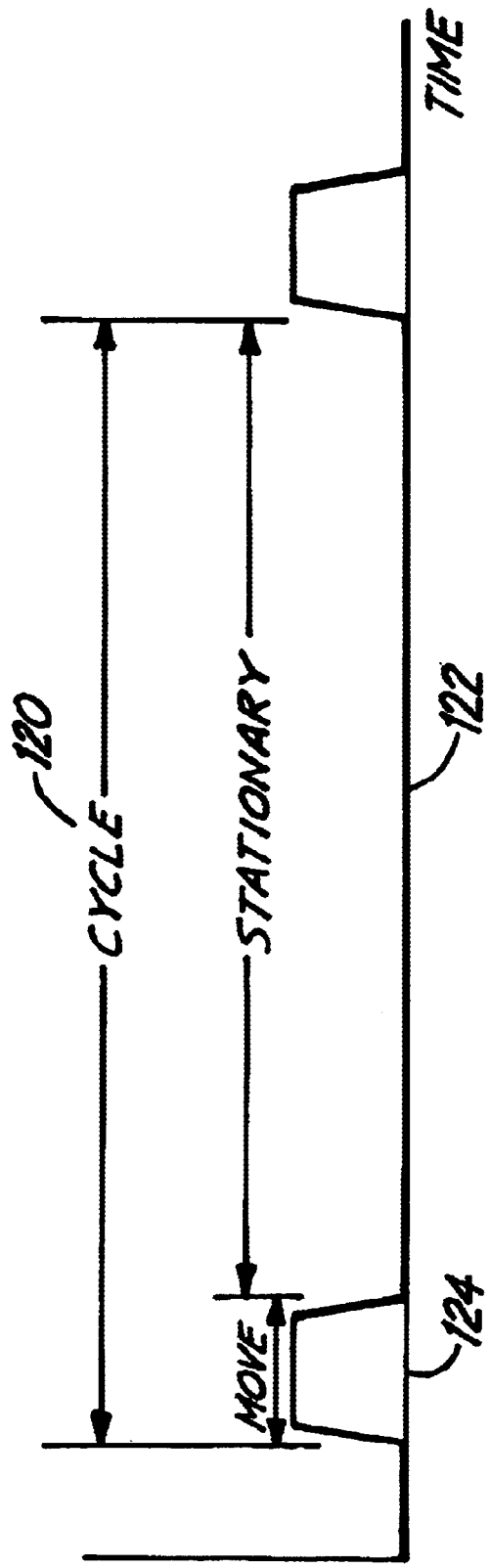
FIG. 12 is a diagram of the timing of thermoforming packaging system cycles.

FIG. 12 is a diagram of the timing of thermoforming packaging system cycle 120. The heating station requires three to six seconds of stationary time 122 to heat the thermoplastic sheet sufficiently to soften it. Once the stationary heating cycle is complete, the mechanical conveyor moves the heated section quickly as indicated at 124 to a forming station where vacuum and/or air pressure is used to force the softened sheet into a mold to create the desired shape. Contact with the mold cools the tray quickly so that a matched stationary three to six second cooling stationary time 122 is sufficient to complete the tray forming process.

While it would be possible to separate the formed trays at this point, it is generally advantageous to continue to mechanically hold and feed the trays through the packaging system for subsequent filling and sealing steps. For purposes of capacity and efficiency, multiple trays are typically formed in each cycle 120, so for example as many as nine trays may be formed in each forming cycle 120. The majority of the time is spent with the conveyor stationary while heating and cooling steps are completed (during stationary time 122).

The effectiveness of thermoforming MAP systems is heavily dependent on the positive and precise control of the position and movement of the formed trays as they are moved from station to station in the packaging process. Each station that performs a processing step on the trays is synchronized to the movement of the conveyor. Due to the thermal characteristics of the thermoplastic tray material, the material is stationary the majority of the time. Since the conveyor must move according to the cycle profile shown in FIG. 12, each subsequent processing station must operate with material movement in exactly the same way. In particular, an irradiation station that is an integrated part of the MAP system must be able to irradiate the material trays during the stationary time 122 of the material movement method of FIG. 12.

While it might be possible to irradiate trays during move time 124 employing an irradiation system according to FIG. 12, it would be quite inefficient. The irradiation system capacity would have to be sized to be able to expose the material to the desired dose in approximately 20% or less of the total processing cycle, which would require a power level of 500% or higher than the continuously moving equivalent. Alternatively, move time 124 of cycle 120 could be extended to match stationary time 122, but this would significantly reduce the capacity of the entire system. An effective irradiation system for a thermoformed tray packaging system therefore should irradiate the materials while they are stationary.

Figure 13:
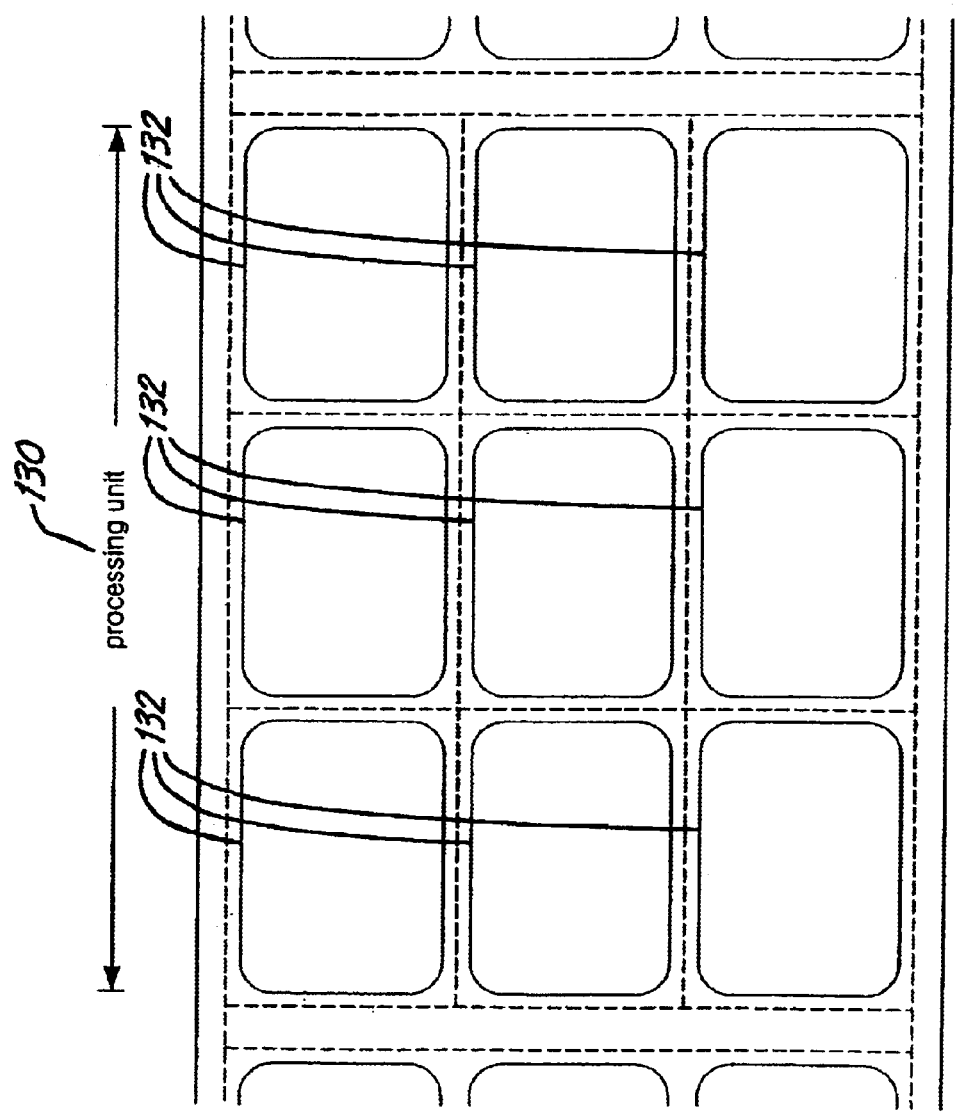
FIG. 13 is a diagram of a basic processing unit of a thermoformed tray packaging system.

FIG. 13 is a diagram of basic processing unit 130 of a thermoformed tray packaging system, carrying nine thermoformed trays 132. An effective irradiation scheme for this type of packaging system must be capable of irradiating materials carried by all nine trays 132 of processing unit 130. Such an irradiation scheme and system is described below.

Figure 14:
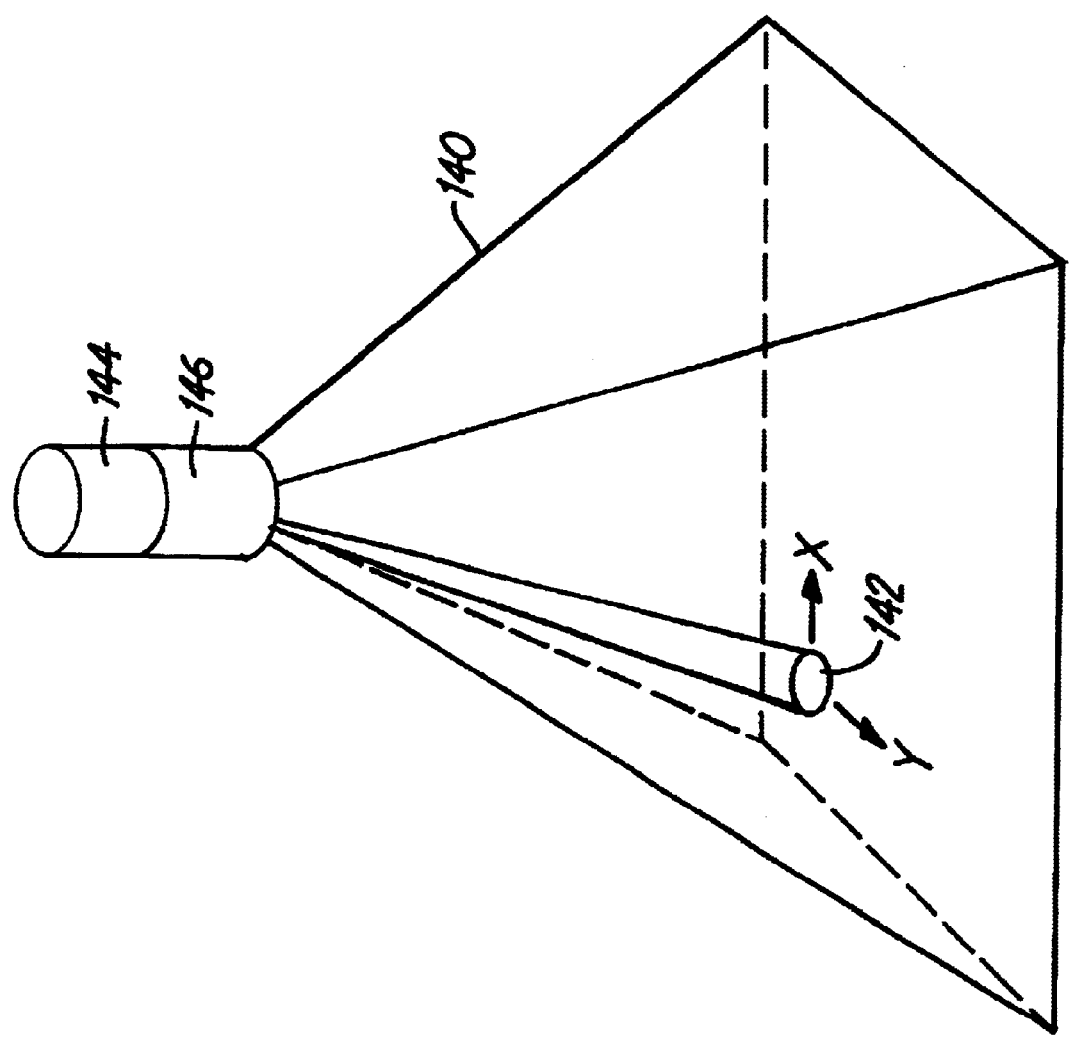
FIG. 14 is a diagram of a rectangular scan horn configured to deflect a radiation beam spot in both x and y directions.

FIG. 14 is a diagram of rectangular scan horn 140 configured to deflect radiation beam spot 142 in both x and y directions. A linear accelerator (not shown) is coupled to scan horn 140 through quadrupole magnet 144 that shapes beam spot 142 into a circular or elliptical shape. Shaped spot 142 is deflected in the x and y directions by respective x and y deflection magnets 146 that are controlled by a computer interfaced to current amplifiers to generate the deflection current necessary to direct the electrons to the desired locations.

Figure 15:
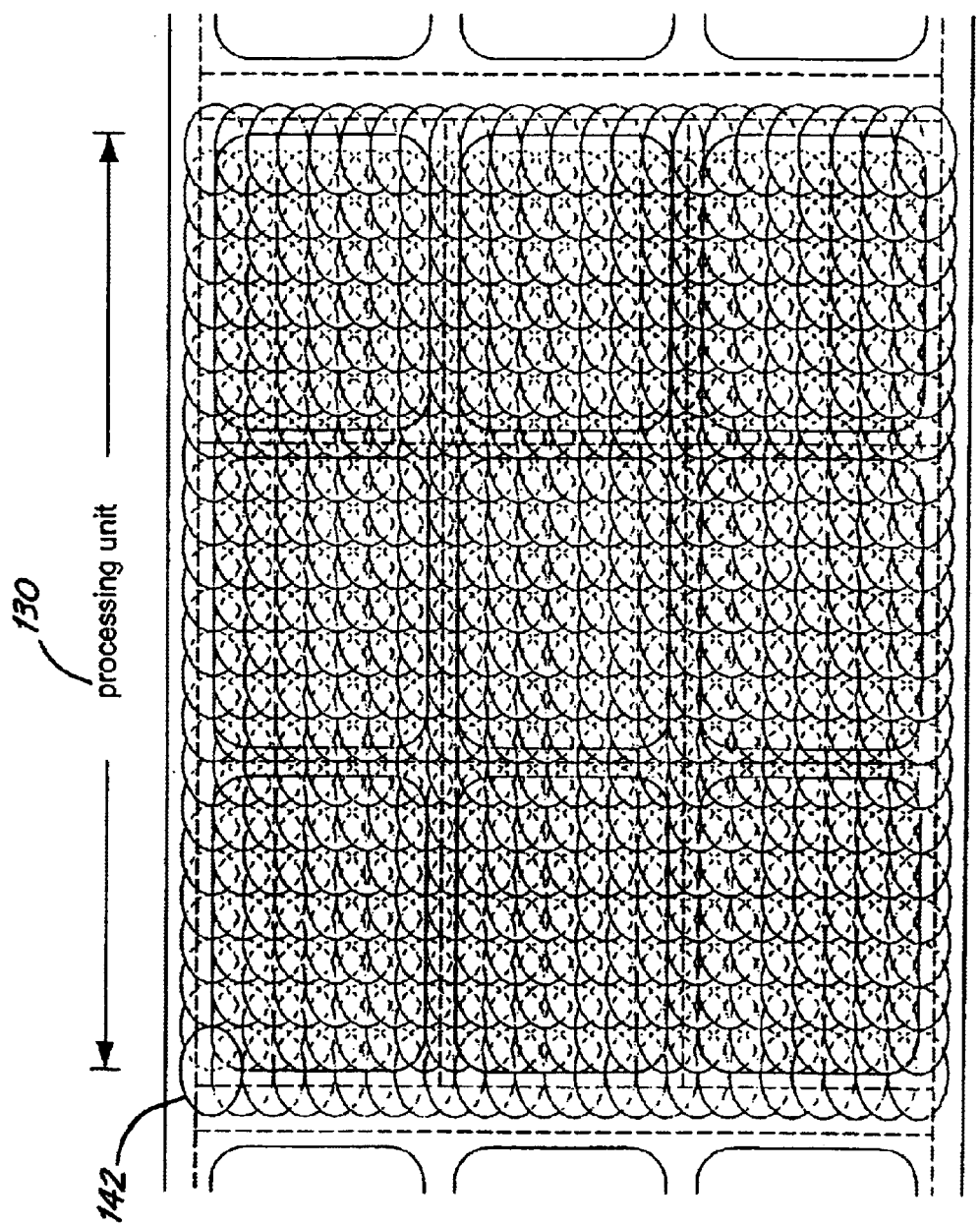
FIG. 15 is a diagram illustrating an exemplary two-dimensional pattern of exposure of material such as a basic processing unit of a thermoformed tray packaging system.

FIG. 15 is a diagram illustrating an exemplary pattern of exposure of material such as processing unit 130. Processing unit 130 is exposed by a series of overlapping horizontal and vertical spots 142. Since the material is not moving during exposure, the positioning of the irradiation exposure spots 142 requires two-dimensional deflection and positioning of the beam paths from the linear accelerator to the material being processed. This is accomplished by rectangular scan horn 140 using horizontal and vertical deflection magnets 146 operated under computer control, as described above with respect to FIG. 14. The rectangular scan area must be physically as large as the largest area to be processed, which might be approximately 60 cm by 60 cm in an exemplary embodiment. The time available for exposure, the area to be exposed and the required dose to be delivered to the material will determine the power required from the linear accelerator. Conversely, for a linear accelerator with a given available power, the area and dose requirement would determine how long it would take to expose the material. In an integrated in-line system, this would determine the stationary time for the entire system.

The computer control of the spot position maybe employed to apply the radiation exposure to a selected subset of the total area available to the two-dimensional scan system. This may be preferred in embodiments where the material to be processed is in trays that have subdivided areas that are filled with dissimilar materials. For example, it maybe desirable to package a group of related but dissimilar foods in the same tray structure for associative marketing purposes.

Figure 16:
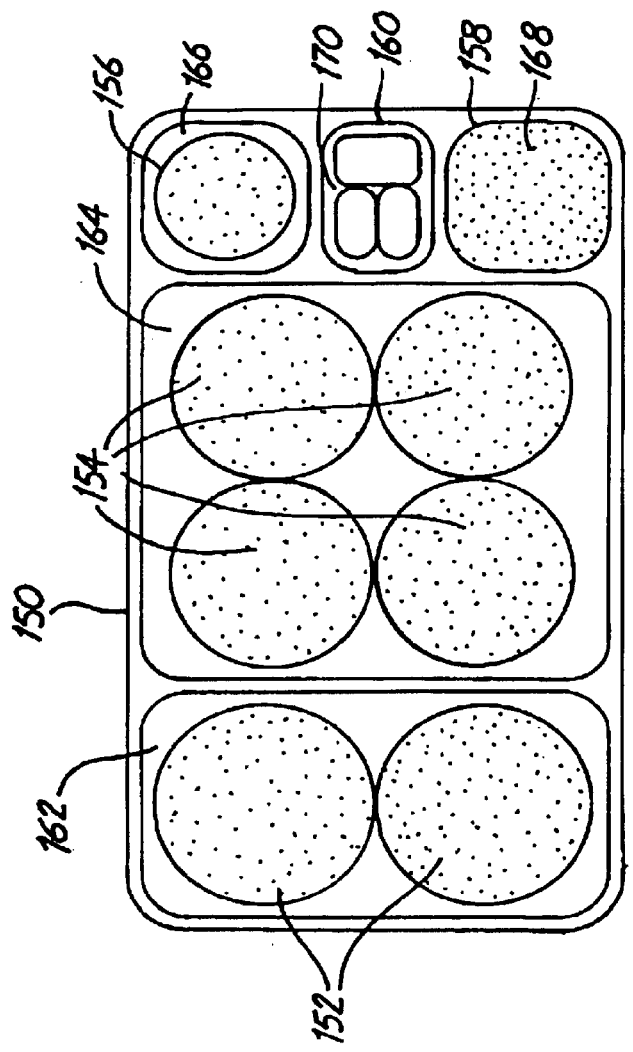
FIG. 16 is a top view of a "ready-to-cook" multi-partition tray carrying various types of food items.
Figure 17:
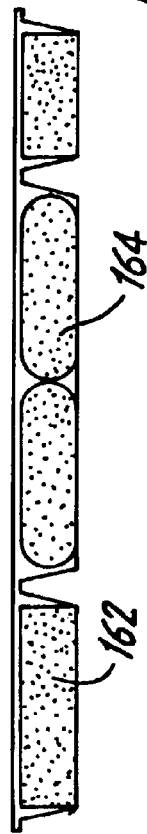
FIG. 17 is a cross-sectional view of the "ready-to-cook" multi-partition tray shown in FIG. 16.

FIG. 16 is a top view, and FIG. 17 is a cross-sectional view, of "ready-to-cook" multi-partition tray 150 carrying fresh ground beef patties 152, buns 154, tomato slices and onions 156, lettuce 158 and condiments 160 (such as pickles, ketchup, and mustard, for example). The fresh ground beef patties 152 are to be irradiated at a first dose level to eliminate E. Coli, the vegetables (tomato slices and onions 156 and lettuce 158) are to be irradiated at a second dose level to extend shelf life by reducing the population of spoilage bacteria, and the remaining food items might receive little or no irradiation dose because of their minimal food safety or preservation needs. In the exemplary embodiment shown in FIGS. 16 and 17, fresh ground beef patties 152 are placed in recessed tray area 162, buns 154 are placed in separate recessed tray area 164, fresh tomato slices and onions 156 are placed in recessed tray area 166, fresh shredded lettuce 158 is placed in recessed area 168 and packaged condiments 160 are placed in recessed tray area 170.

Figure 18:
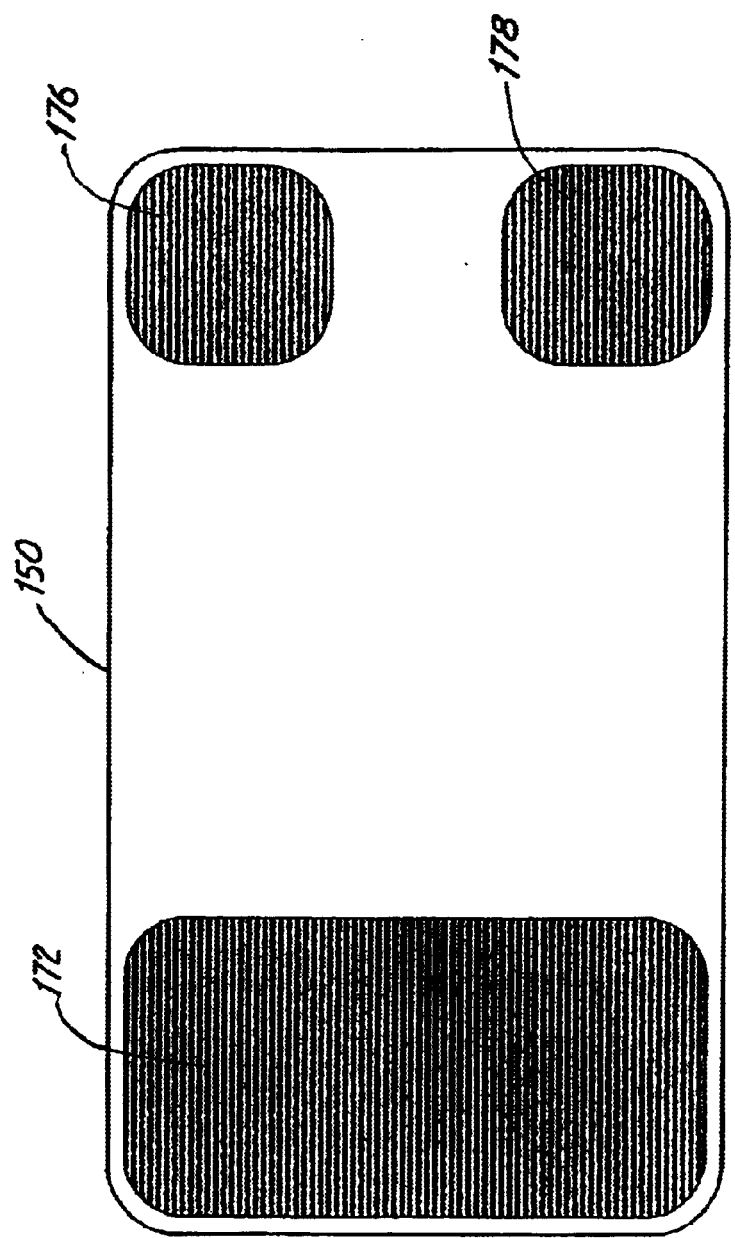
FIG. 18 illustrated an irradiation pattern that may be selectively applied to particular areas of the multi-partition tray shown in FIG. 16.

FIG. 18 illustrates the regional irradiation pattern that may be selectively applied to particular areas of tray 150. Region 172 (corresponding to recessed tray area 162 of FIG. 16) may be irradiated with a dose level appropriate for fresh ground beef such as 1.5 kGy in an exemplary embodiment. Regions 176 and 178 (corresponding to respective recessed tray areas 166 and 168) may be irradiated with a dose level of appropriate for fresh vegetable shelf life extension such as 500 Gy in an exemplary embodiment.

Figure 19:
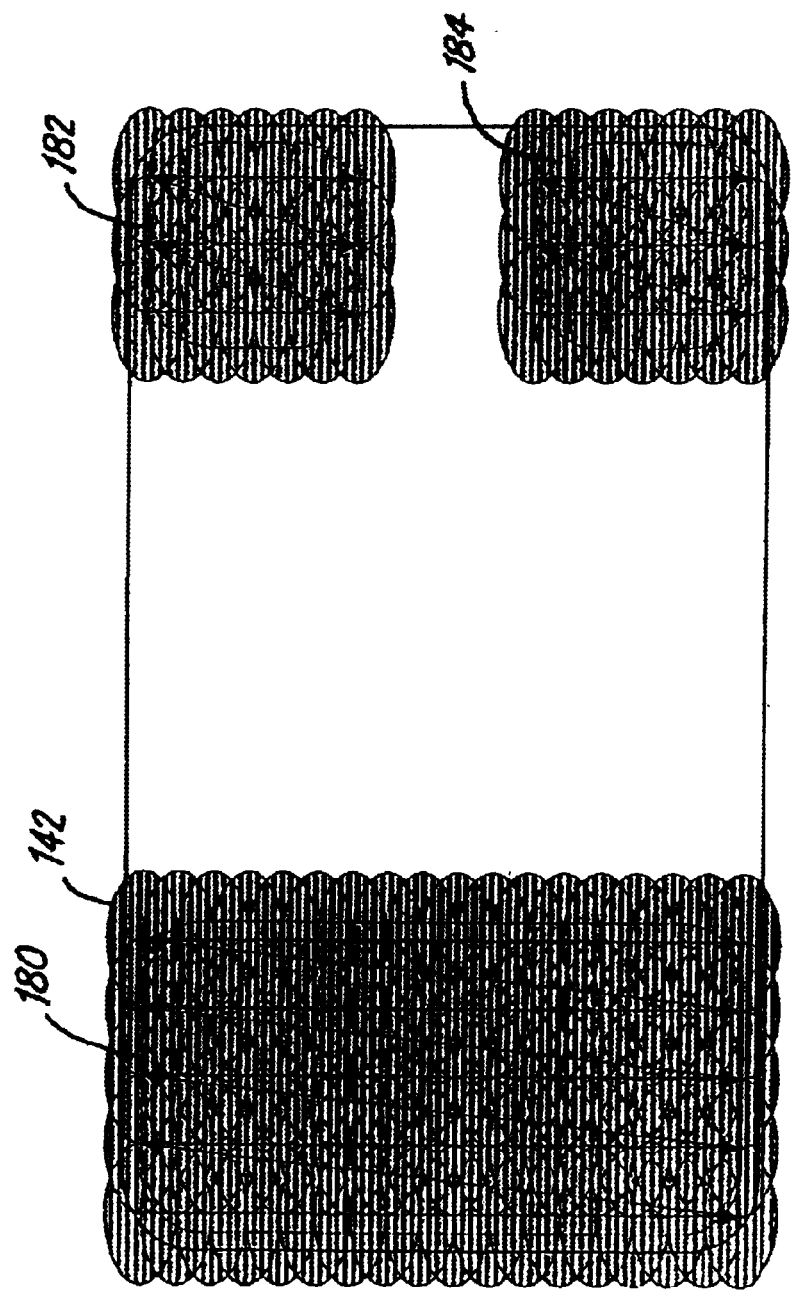
FIG. 19 is a diagram of an irradiation scheme in which radiation is applied by positioning beam spots under computer control to expose areas in overlapping fashion.

FIG. 19 is a diagram of an irradiation scheme according to the present invention in which radiation is applied by positioning spots 142 under computer control to expose particular areas 180, 182 and 184 (which include respective regions 172, 176 and 178 of FIG. 18) in overlapping fashion. Each area may receive a specific dose as required for the food material to be exposed as previously described. To achieve dosage uniformity, spots 142 must not only overlap, but spots near the edge of the food material regions must overlap past the edge of the food material region borders (as shown in FIG. 19). This overlap past the edge of the food material region borders has the potential to expose food materials that either should not be irradiated, or should be irradiated at lower dosage levels, unless appropriate precautions are taken.

Figure 20:
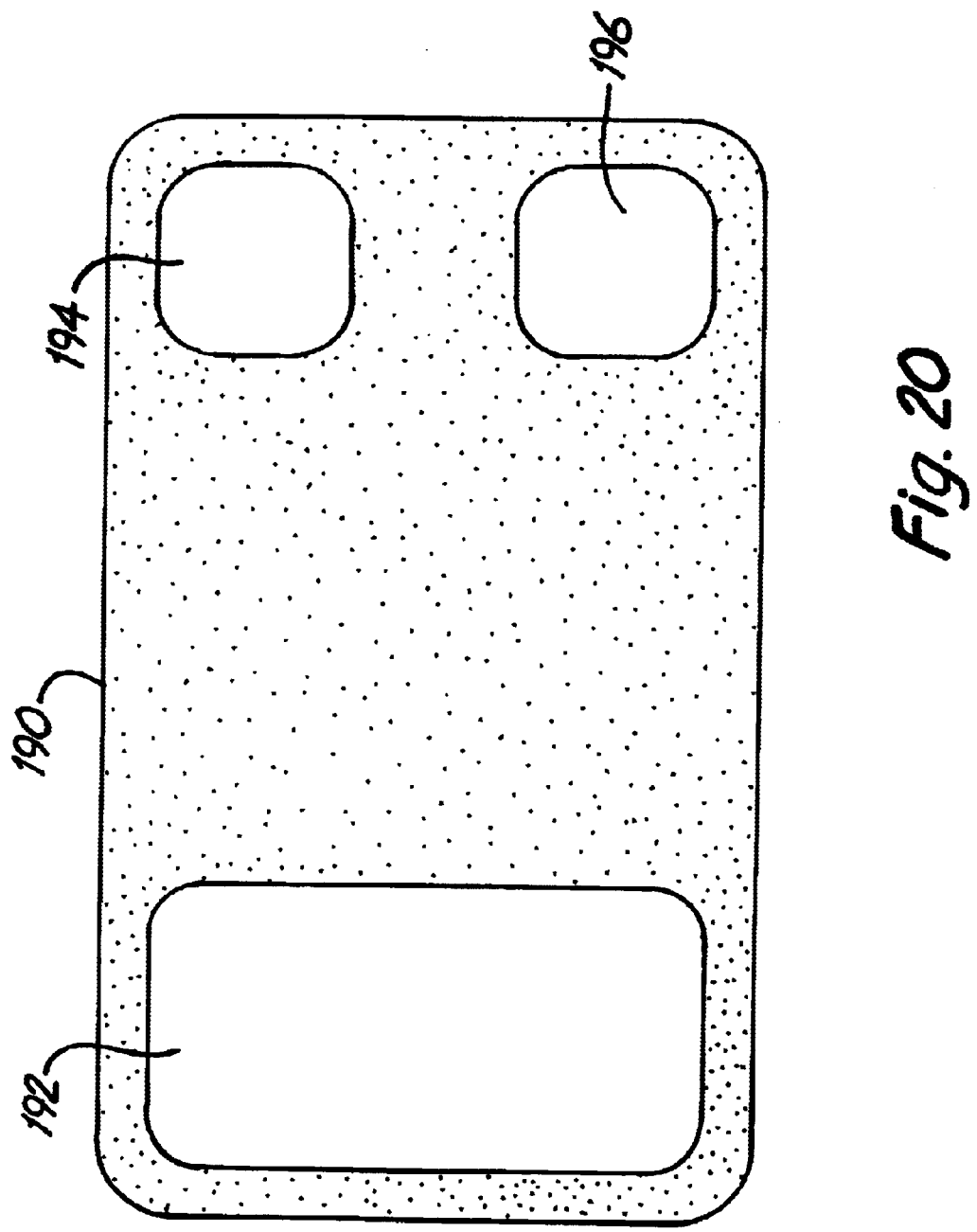
FIG. 20 is a diagram illustrating a mask for placement over a tray of food materials to be irradiated, with apertures disposed over the areas that are to receive radiation exposure.

FIG. 20 is a diagram illustrating mask 190 that is placed over a tray of food materials to be irradiated, with apertures disposed over the areas that are to receive radiation exposure. Mask 190 ensures that food materials that should not be irradiated or that should be irradiated at lower dosage levels are not overexposed by radiation that overlaps food material borders. For the example given above, aperture 192 corresponds to the area that contains fresh ground beef patties, aperture 194 corresponds to the area containing tomato and onion slices, and aperture 196 corresponds to the area containing fresh shredded lettuce.

In systems that form trays using a thermoforming process, the location of the trays is quite precisely controlled. Mask 190 is physically located with apertures 192, 194 and 196 placed exactly over the areas that are to receive radiation. The actual dose may be specified for each area. The areas that are not to be exposed are protected by the shielding effect of mask 190, which may be constructed of an absorbing material such as an appropriate metal. The absorption does not have to be as effective as radiation shielding material to manage adjacent exposure, so the metal material may be aluminum or stainless steel of approximately 0.5 to 1.0 cm. thickness in an exemplary embodiment. Provision for cooling mask 190 may be required to dissipate the heat caused by the radiation power absorption. This may be implemented with liquid cooling tubes attached to the mask plate 190 to conduct heat away from the plate, for example. Other cooling schemes will be apparent to one skilled in the art.

Figure 21:
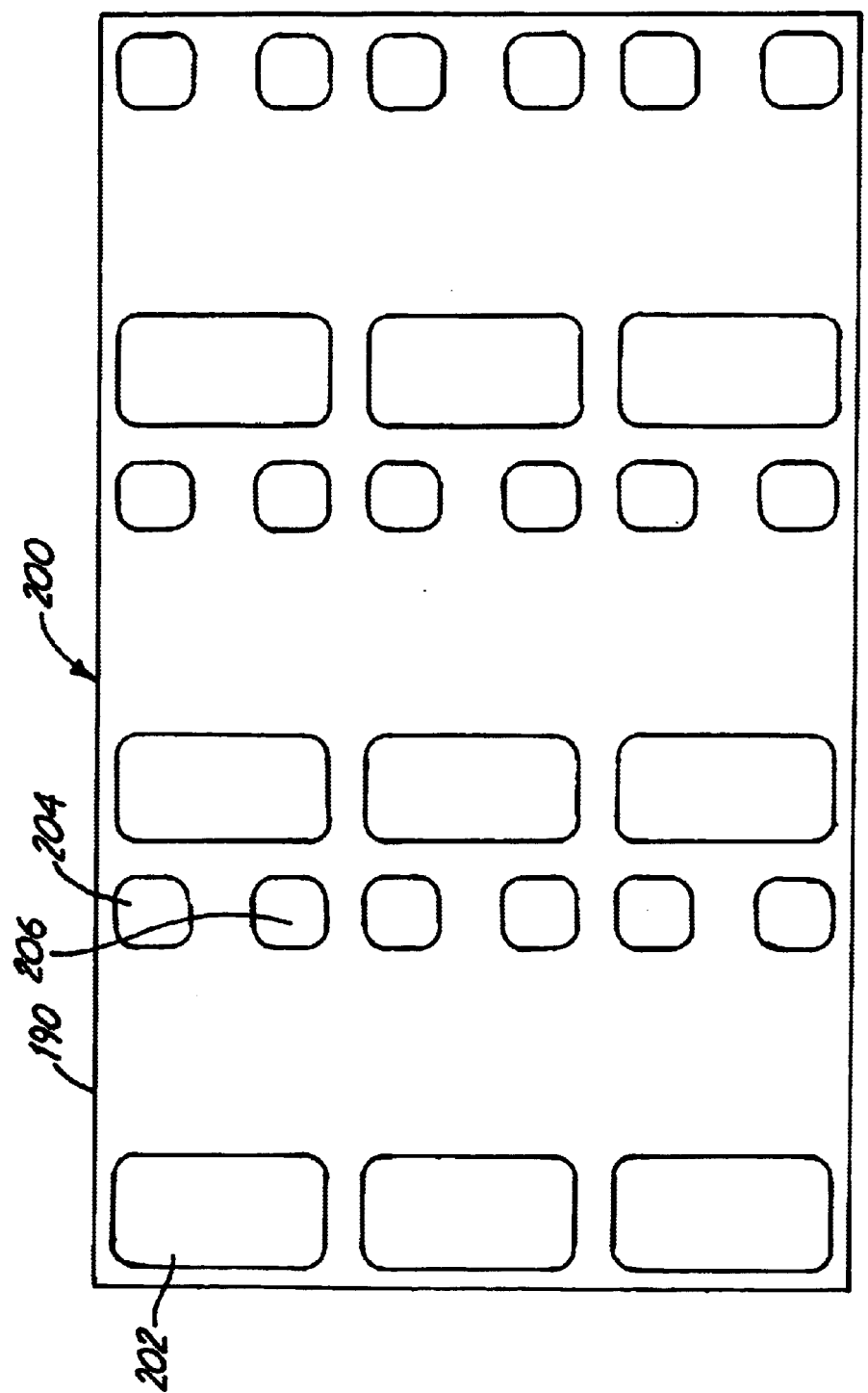
FIG. 21 is a diagram illustrating a multi-tray processing configuration having apertures disposed for each portion of the trays that are processed as a single unit during the stationary dwell time of a thermoforming packaging system.

A plurality of masks similar to mask 190 may be designed for each particular configuration of dissimilar food products to be processed. FIG. 21 is a diagram illustrating multi-tray processing unit configuration 200 having apertures 202, 204 and 206 disposed for each portion of nine trays that are processed as a single unit during the stationary dwell time of a thermoforming packaging system. This mask technique could also be applied with an ordinary scanning irradiation exposure method such as is described above with respect to the irradiation systems disclosed in FIGS. 1–11.

In most embodiments, it is preferable to couple mask 190 with the computer controlled positioning of exposure spots 142 so that mask 190 need only absorb the beam power associated with the edge overlap. In the example illustrated by FIG. 21, the beam utilization may be optimized by 200% or more by directing spots 142 to aperture areas 202, 204 and 206 and not to areas that would only be absorbed by mask 190.

The previously described multiple area trays may be configured to accommodate a widely varying set of dissimilar food items that may be associated together. Irradiation may be applied with independently set dose levels for any area in the tray. The quality of the food may be maintained at optimum levels by removing the oxygen in the irradiation chamber during the exposure process. The actual package atmosphere may be modified per the standard process methodology utilized in MAP systems. To maintain sanitation and prevent the possibility of recontamination of the food material after irradiation and before final packaging, an enclosing "clean cabinet" may be interposed between the irradiation system and the MAP packaging equipment.

Figure 22:
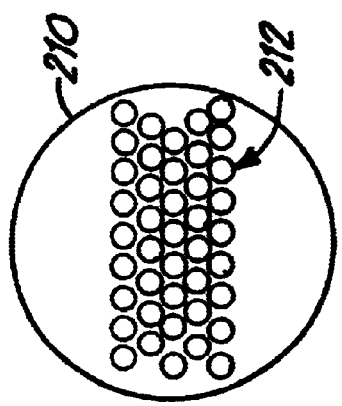
FIG. 22 is a diagram of an exemplary grinding plate.

One method of forming ground beef into appropriate shapes or "loaves" for packaging on preformed or thermoformed trays involves forcing the ground beef through a grinding plate. FIG. 22 is a diagram of exemplary grinding plate 210. Grinding plate 210 includes aperture pattern 212 through which ground beef emerges in the shape of "noodles." The noodles of ground beef are expanded at grinding plate 210 and have small spaces between them, but settle together after exiting hole pattern 212 of grinding plate 210 to form the desired loaf shape and thickness.

When the noodles of ground beef settle together to form a loaf shape, oxygen can be trapped between the noodles in the loaf. In an irradiation system that operates in a modified atmosphere that excludes oxygen, the trapped oxygen in the ground beef loaf itself can subvert the purpose of excluding oxygen in the irradiation system, which is to prevent lipid oxidation effects during irradiation. It is therefore important in such a system to ensure that oxygen is not trapped within the ground beef loaves that are formed by a grinder before being input to the modified atmosphere irradiation system.

Figure 23:
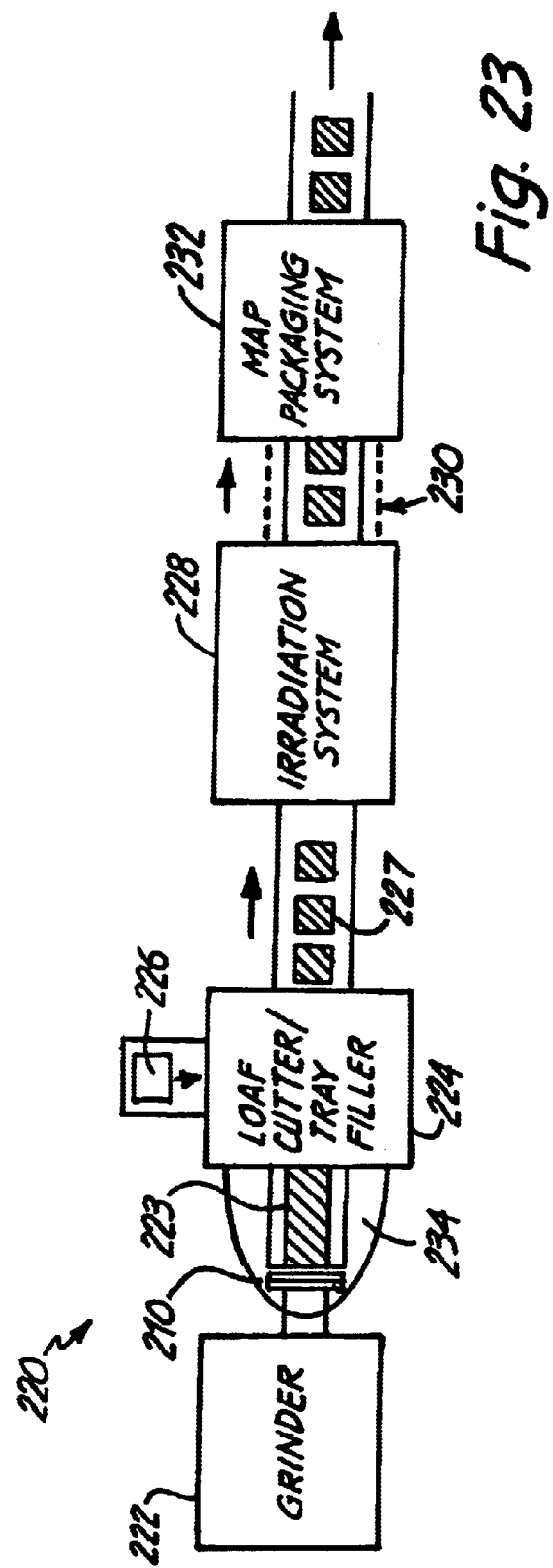
FIG. 23 is a diagram illustrating a ground beef processing system that controls the atmosphere throughout the system.

FIG. 23 is a diagram illustrating ground beef processing system 220 that controls the atmosphere throughout the system. Beef (or other food material to be processed) is loaded into grinder 222, which grinds the beef and forces it through grinding plate 210. The ground beef emerges through grinding plate in a "ribbon" shape, and is operated on in loaf cutter/tray filler 224 to place the ground beef into trays 226 in an appropriate manner. The filled trays are then input to irradiation system 228, which may be implemented according to any of the exemplary embodiments described above, operating in a modified atmosphere environment to exclude oxygen. Irradiated beef trays pass on through clean cabinet 230 to modified atmosphere packaging system 232, which typically operates in a high oxygen environment. Finally, packaged product is output by packaging system 232.

In order to prevent oxygen from being trapped in the ground beef as it exits through grinding plate 210, controlled atmosphere shroud 234 is provided to enclose grinding plate 210 and the path for ground beef traveling between grinding plate 210 and loaf cutter/tray filler 224. Controlled atmosphere shroud 234 therefore provides an environment where oxygen may be excluded, such as by filling the shrouded area with nitrogen, in the area where noodles of ground beef settle into a ribbon shape. Only gases present in the modified atmosphere within shroud 234 will be trapped within the ribbon and the subsequently cut loaves of ground beef, which ensures that oxygen will not be trapped in the ground beef loaves when they are irradiated in the controlled atmosphere of irradiation system 228.

In the embodiments of the invention described above, the modification of the atmosphere has been universally described as excluding oxygen, in order to prevent undesired lipid oxidation effects while irradiating food articles such as ground beef. However, it will be understood by those skilled in the art that the ability of the present invention to modify the atmosphere inside the irradiation system is not limited to only the exclusion of oxygen, but could be utilized to achieve any desired atmospheric conditions that are different from the ambient atmosphere.

The above-described invention provides a number of advantageous features of an irradiation system for effectively processing food and other materials. A sealed conduit encloses at least a processing portion of a conveying system, providing the ability to modify the atmosphere inside the sealed conduit. A gas such as nitrogen may be introduced into the sealed conduit to exclude oxygen that may cause undesired lipid oxidation during irradiation of food materials. The interior of the sealed conduit may also be industrially cleaned in an efficient manner. These and other features disclosed above provide excellent performance in a system for irradiating food and other articles.

Although the present invention has been described with reference to preferred embodiments, workers skilled in the art will recognize that changes may be made in form and detail without departing from the spirit and scope of the invention.

What is claimed is:

1. An irradiation system comprising:
    a conveying system for moving material to be irradiated through a processing area; an irradiation source for applying radiation comprising at least one of an electron beam, x-rays and gamma rays to material in the processing area; and
    a sealed conduit enclosing the conveying system in at least the processing area, the sealed conduit having a controlled interior atmosphere that excludes oxygen.

2. The irradiation system of claim 1, wherein the conveying system comprises at least one powered conveyor for carrying the material to be irradiated through the processing area.

3. The irradiation system of claim 1, wherein the interior atmosphere of the sealed conduit is filled with a gas selected from the group consisting of nitrogen and carbon dioxide.

4. The irradiation system of claim 1, wherein the irradiation source is configured and arranged to direct radiation onto material in the processing area from two opposite sides.

5. The irradiation system of claim 1, wherein the sealed conduit is composed of food contactable material having a thickness of no greater than 0.125 inches.

6. The irradiation system of claim 1, further comprising:
a shielding structure around the irradiation source and the sealed conduit configured and arranged to obstruct a path for radiation to escape from the processing area.

7. The irradiation system of claim 6, wherein the shielding structure includes a mechanism for allowing removal of the conveying system in the processing area.

8. The irradiation system of claim 1, wherein the conveying system comprises:
an input conveyor for carrying material into the irradiation system at a first elevation;
an input elevator receiving the material from the input conveyor and carrying the material to a second elevation;
a process conveyor receiving the material from the input elevator and carrying the material through the processing area at the second elevation;
an output elevator receiving the material from the process conveyor and carrying the material to a third elevation; and
an output conveyor receiving the material from the output elevator and carrying the material out of the irradiation system at the third elevation.

9. The irradiation system of claim 1, wherein the conveying system comprises:
an input conveyor for carrying material into the irradiation system at a first elevation;
an input ramp providing a path for the material to move from the first elevation to a second elevation;
a process conveyor receiving the material from the input ramp and carrying the material through the processing area at the second elevation;
an output ramp providing a path for the material to move from the second elevation to a third elevation; and
an output conveyor receiving the material from the output ramp and carrying the material out of the irradiation system at the third elevation.

10. The irradiation system of claim 9, wherein the input ramp and the output ramp each comprise a powered conveyor.

11. The irradiation system of claim 1, wherein the conveying system comprises:
a first conveyor mechanism for carrying containers of material through the processing area; and
a second conveyor mechanism for carrying loose material through the processing area.

12. A food processing system comprising:
a conveying system for moving food through a processing area;
an irradiation source for applying radiation comprising at least one of an electron beam, x-rays and gamma rays to food in the processing area;
a sealed conduit enclosing the conveying system in the processing area, an interior of the sealed conduit having a first controlled atmosphere for irradiation; and a packaging system located downstream from the processing area for packaging irradiated food in a second controlled atmosphere for packaging.

13. The food processing system of claim 12, wherein the conveying system includes at least one powered conveyor for carrying the food through the processing area.

14. The food processing system of claim 12, wherein the first controlled atmosphere excludes oxygen.

15. The food processing system of claim 14, wherein the interior atmosphere of the sealed conduit is filled with a gas selected from the group consisting of nitrogen and carbon dioxide.

16. The food processing system of claim 12, wherein the second controlled atmosphere is high in oxygen.

17. The food processing system of claim 12, wherein the irradiation source is configured and arranged to direct radiation onto material in the processing area from two opposite sides.

18. The food processing system of claim 12, wherein the sealed conduit is composed of food contactable material having a thickness of no greater than 0.125 inches.

19. The food processing system of claim 12, further comprising:
a shielding structure around the irradiation source and the sealed conduit configured and arranged to obstruct a path for radiation to escape from the processing area.

20. The food processing system of claim 19, wherein the shielding structure includes a mechanism for allowing removal of the conveying system in the processing area.

21. The food processing system of claim 12, wherein the conveying system comprises:
an input conveyor for carrying material at a first elevation;
an input elevator receiving the material from the input conveyor and carrying the material to a second elevation;
a process conveyor receiving the material from the input elevator and carrying the material through the processing area at the second elevation;
an output elevator receiving the material from the process conveyor and carrying the material to a third elevation; and
an output conveyor receiving the material from the output elevator and carrying the material to the packaging system at the third elevation.

22. The food processing system of claim 12, wherein the conveying system comprises:
an input conveyor for carrying material at a first elevation;
an input ramp providing a path for the material to move from the first elevation to a second elevation;
a process conveyor receiving the material from the input ramp and carrying the material through the processing area at the second elevation;
an output ramp providing a path for the material to move from the second elevation to a third elevation; and
an output conveyor receiving the material from the output ramp and carrying the material to the packaging system at the third elevation.

23. The food processing system of claim 22, wherein the input ramp and the output ramp each comprise a powered conveyor.

24. A food processing system comprising:
a grinder providing ground meat through a grinding plate located within a shroud having an interior atmosphere that excludes oxygen, wherein the ground meat exits the grinding plate in a ribbon form;

a loading system for placing the ground meat onto trays;

an irradiation system receiving trays of ground meat from the loading system and exposing the trays of ground meat to radiation comprising at least one of an electron beam, x-rays and gamma rays in a first controlled atmosphere; and a packaging system receiving irradiated trays of ground meat from the irradiation system and packaging the trays of ground meat in a second controlled atmosphere.

25. The food processing system of claim 24, wherein the first controlled atmosphere excludes oxygen.

26. The food processing system of claim 25, wherein the first controlled atmosphere is filled with a gas selected from the group consisting of nitrogen and carbon dioxide.

27. The food processing system of claim 24, wherein the second controlled atmosphere is high in oxygen.

28. A method of irradiation comprising:

conveying material to be irradiated through a processing area; and controlling an atmosphere in the processing area to exclude oxygen; and applying radiation comprising at least one of an electron beam, x-rays and gamma rays to the material in the processing area.

29. The method of claim 28, wherein controlling the atmosphere in the processing area comprises filling the processing area with a gas selected from the group consisting of nitrogen and carbon dioxide.

30. A method of irradiating food comprising:

conveying food to be irradiated through a processing area;

controlling a first atmosphere in the processing area to be different from an ambient atmosphere; applying radiation comprising at least one of an electron beam, x-rays and gamma rays to the food in the processing area; and packaging irradiated food in a second atmosphere that is controlled to be different from the ambient atmosphere.

31. The method of claim 30, wherein controlling the first atmosphere in the processing area comprises excluding oxygen from the processing area.

32. The method of claim 31, wherein controlling the first atmosphere in the processing area comprises filling the processing area with a gas selected from the group consisting of nitrogen and carbon dioxide.

33. The method of claim 30, wherein the second atmosphere is high in oxygen.

* * * * *